(12) United States Patent
Seifer et al.

(10) Patent No.: US 6,518,014 B1
(45) Date of Patent: Feb. 11, 2003

(54) HEPADNAVIRUS CORES

(75) Inventors: Maria Seifer, Middletown, CT (US); Robert Hamatake, Madison, CT (US); David N. Standring, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/890,735

(22) Filed: Jul. 11, 1997

Related U.S. Application Data

(60) Provisional application No. 60/021,561, filed on Jul. 11, 1996.

(51) Int. Cl.$^7$ .......................... C07K 14/02; C12N 7/01; C12Q 1/70
(52) U.S. Cl. ...................... 435/5; 435/320.1; 435/235.1
(58) Field of Search ........................ 435/5, 320.1, 235.1

(56) References Cited

U.S. PATENT DOCUMENTS

| | | | |
|---|---|---|---|
| 5,334,525 A | | 8/1994 | Seeger .......................... 435/194 |
| 5,980,901 A | * | 11/1999 | Shih et al. ................ 424/189.1 |

OTHER PUBLICATIONS

Miller et al., Virology, 1984, vol. 139, pp. 53–63.
Blum et al., Virology, 1984, vol. 139, 87–96.
Chang et al., EMBO Journal, 1987, vol. 6, No. 3, 675–680.
Bartenschlager et al., J. Virol. 64: 5324–5332, 1990.
Birnbaum and Nassal, J. Virol. 64: 3319–3330, 1990.
Christman et al., Proc. Natl. Acad. Sci. USA 79: 1815–1819, 1982.
Hatton et al., J. Virol. 66: 5232–5241, 1992.
Hilditch et al., J. Gen. Virol. 71: 2755–2759, 1990.
Hirsch et al., Nature, 344: 552–555, 1990.
Hirschman et al., Proc. Natl. Acad. Sci. USA 77: 5507–5511, 1980.
Lanford, et al., J. Virol. 69: 4431–4439, 1995.
Lanford and Notvall, Virol. 176: 222–233, 1990.
Jansen et al., Antimicrobial Agents and Chemotherapy 37: 441–447, 1993.
Korba and Milman, *Antiviral Research* 15:217–228, 1991.
Nassal, J. Virol. 66: 4107–4116, 1992.
Oberhaus and Newbold, J. Virol. 69: 5697–5704, 1995.
Radziwill et al., J. Virol. 64:613–620, 1990.
Schlicht et al., J. Virol. 63: 2995–3000, 1989.
Seifer and Standring, Virology 196: 70–78, 1993.
Seifer et al., J. Virol. 67: 249–257, 1993.

(List continued on next page.)

*Primary Examiner*—Michael P. Woodward
*Assistant Examiner*—Lori Clow
(74) *Attorney, Agent, or Firm*—Audrey F. Sher

(57) ABSTRACT

Provided in one embodiment is a non-infectious, recombinant hepadnavirus core particle composition comprising isolated hepadnavirus core particles, template RNA encapsidated in the same core particles and hepadnavirus polymerase encapsidated in the same core particles, wherein, upon addition of deoxynucleoside triphosphates to the composition, the hepadnavirus polymerase incorporates deoxynucleotides from the added deoxynucleosides into reverse transcripts of the template RNA beginning with the first deoxynucleotide of the reverse transcript or within about 10 deoxynucleotides of the first deoxynucleotide of the reverse transcript. Another embodiment provides hapadnaviral core particles with all three functional components: (1) P; (2) C; and (3) a nucleic acid that serves as a template. These core particles include for example (a) recombinant, insect-cell-derived core particles, (b) core particles produced in cells contacted with a reverse transcriptase inhibitor, and (c) core particles that are especially suitable for assays for (+)-strand synthesis.

28 Claims, 4 Drawing Sheets

OTHER PUBLICATIONS

Seifer and Standring, J. Virol. 67: 4513–4520, 1993.
Seifer and Standring, Intervirology 38:295–303, 1995.
Sells et al., Proc. Natl. Acad. Sci. USA 84: 1005–1009, 1987.
Standring et al., UCLA Symp. Mol. Cell. Biol. New Series 70:117–127, 1987.
Tavis and Ganem, Proc. Natl. Acad. Sci. USA 90: 4107–4111, 1993.
Wang and Seeger, J. Virol. 67: 6507–6512, 1993.
Wang and Seeger, Cell 71:663–670, 1992.
Yu and Summers, J. Virol. 65: 2511–2517, 1991.
Ziermann and Ganem, Virology 219: 350–356, 1996.
Zhou and Standring, J. Virol. 65:5457–5464, 1991.

* cited by examiner

1 AATTCCACAA CCTTCCACCA AACTCTGCAA GATCCCAGAG TGAGAGGCCT GTATTTCCCT
 61 GCTGGTGGCT CCAGTTCAGG AACAGTAAAC CCTGTTCTGA CTACTGCCTC TCCCTTATCG
121 TCAATCTTCT CGAGGATTGG GGACCCTGCG CTGAACATGG AGAACATCAC ATCAGGATTC
181 CTAGGACCCC TTCTCGTGTT ACAGGCGGGG TTTTTCTTGT TGACAAGAAT CCTCACAATA
                       3'-CCGCCCC AAAAAGATCA TCTGTTCTTA GG-5'
                                          RH101
241 CCGCAGAGTC TAGACTCGTG GTGGACTTCT CTCAATTTTC TAGGGGAAC TACCGTGTGT
301 CTTGGCCAAA ATTCGCAGTC CCCAACCTCC AATCACTCAC CAACCTCTTG TCCTCCAACT
361 TGTCCTGGTT ATCGCTGGAT GTGTCTGCGG CGTTTTATCA TCTTCCTCTT CATCCTGCTG
                                                                3'-C
                                                                RH102
421 CTATGCCTCA TCTTCTTGTT GGTTCTTCTG GACTATCAAG GTATGTTGCC CGTTTGTCCT
    GATACGGAGT AGAAGATCAT CCAAGAAGAC C-5'
           RH102 (continued)
481 CTAATTCCAG GATCCTCAAC AACCAGCACG GGACCATGCC GGACCTGCAT GACTACTGCT
541 CAAGGAACCT CTATGTATCC CTCCTGTTGC TGTACCAAAC CTTCGGACGG AAATTGCACC
601 TGTATTCCCA TCCCATCATC CTGGGCTTTC GGAAAATTCC TATGGGAGTG GGCCTCAGCC
661 CGTTTCTCCT GGCTCAGTTT ACTAGTGCCA TTTGTTCAGT GGTTCGTAGG GCTTTCCCCC
721 ACTGTTTGGC TTTCAGTTAT ATGGATGATG TGGTATTGGG GCCAAGTCT GTACAGCATC
781 TTGAGTCCCT TTTTACCGCT GTTACCAATT TTCTTTTGTC TTTGGGTATA CATTTAAACC
841 CTAACAAAAC AAAGAGATGG GGTTACTCTC TAAATTTAT GGGTTATGTC ATTGGATGTT
901 ATGGGTCCTT GCCACAAGAA CACATCATAC AAAAAATCAA AGAATGTTTT AGAAAACTTC
961 CTATTAACAG GCCTATTGAT TGGAAAGTAT GTCAACGAAT TGTGGGTCTT TTGGGTTTTG
1021 CTGCCCCTTT TACACAATGT GGTTATCCTG CGTTGATGCC TTTGTATGCA TGTATTCAAT
1081 CTAAGCAGGC TTTCACTTTC TCGCCAACTT ACAAGGCCTT TCTGTGTAAA CAATACCTGA
1141 ACCTTTACCC CGTTGCCCGG CAACGGCCAG GTCGTGCCA AGTGTTTGCT GACGCAACCC
1201 CCACTGGCTG GGGCTTGGTC ATGGGCCATC AGCGCATGCG TGGAACCTTT TCGGCTCCTC
1261 TGCCGATCCA TACTGCGGAA CTCCTAGCCG CTTGTTTTGC TCGCAGCAGG TCTGGAGCAA
1321 ACATTATCGG GACTGATAAC TCTGTTGTCC TATCCCGCAA ATATACATCG TTTCCATGGC
1381 TGCTAGGCTG TGCTGCCAAC TGGATCCTGC GCGGGACGTC CTTTGTTTAC GTCCCGTCGG
1441 CGCTGAATCC TGCGGACGAC CCTTCTCGGG GTCGCTTGGG ACTCTCTCGT CCCCTTCTCC
1501 GTCTGCCGTT CCGACCGACC ACGGGGCGCA CCTCTCTTTA CGCGGACTCC CCGTCTGTGC
1561 CTTCTCATCT GCCGGACCGT GTGCACTTCG CTTCACCTCT GCACGTCGCA TGGAGACCAC
                                     DR2
1621 CGTGAACGCC CACCAAATAT TGCCCAAGGT CTTACATAAG AGGACTCTTG GACTCTCAGC
1681 AATGTCAACG ACCGACCTTG AGGCATACTT CAAAGACTGT TTGTTTAAAG ACTGGGAGGA
1741 GTTGGGGGAG GAGATTAGGT TAAAGGTCTT TGTACTAGGA GGCTGTAGGC ATAAATTGGT
1801 CTGCGCACCA GCACCATGCA ACTTTTTCAC CTCTGCCTAA TCATCTCTTG TTCATGTCCT
                                                       SS SSSSSSSSS
                              DR1
1861 ACTGTTCAAG CCTCCAAGCT GTGCCTTGGG TGGCTTTGGG GCATGGACAT CGACCCTTAT
     SBBBBBBSSS SSSSSSSSLL LLLLSSSSSS MSSSSSSSSS SSSSSSSSS
                   (continued)
1921 AAAGAATTTG GAGCTACTGT GGAGTTACTC TCGTTTTTGC CTTCTGACTT CTTTCCTTCA
1981 GTACGAGATC TTCTAGATAC CGCCTCAGCT CTGTATCGGG AAGCCTTAGA GTCTCCTGAG
2041 CATTGTTCAC CTCACCATAC TGCACTCAGG CAAGCAATTC TTTGCTGGGG GGAACTAATG
2101 ACTCTAGCTA CCTGGGTGGG TGTTAATTTG GAAGATCCAG CGTCTAGAGA CCTAGTAGTC
2161 AGTTATGTCA ACACTAATAT GGGCCTAAAG TTCAGGCAAC TCTTGTGGTT TCACATTTCT
2221 TGTCTCACTT TTGGAAGAGA AACAGTTATA GAGTATTTGG TGTCTTTCGG AGTGTGGATT
2281 CGCACTCCTC CAGCTTATAG ACCACCAAAT GCCCTATCC TATCAACACT TCCGGAGACT
2341 ACTGTTGTTA GACGACGAGG CAGGTCCCCT AGAAGAAGAA CTCCCTCGCC TCGCAGACGA
2401 AGGTCTCAAT CGCCGCGTCG CAGAAGATCT CAATCTCGGG AATCTCAATG TTAGTATTCC
2461 TTGGACTCAT AAGGTGGGGA ACTTTACTGG GCTTTATTCT TCTACTGTAC CTGTCTTTAA
2521 TCCTCATTGG AAAACACCAT CTTTTCCTAA TATCATTTA CACCAAGACA TTATCAAAAA
2581 ATGTGAACAG TTTGTAGGCC CACTCACAGT TAATGAGAAA AGAAGATTGC AATTGATTAT
2641 GCCTGCCAGG TTTTATCCAA AGGTTACCAA ATATTTACCA TTGGATAAGG GTATTAAACC
2701 TTATTATCCA GAACATCTAG TTAATCATTA CTTCCAAACT AGACACTATT TACACACTCT
2761 ATGGAAGGCG GGTATATTAT ATAAGAGAGA AACAACACAT AGCGCCTCAT TTTGTGGGTC

FIG. 2A

```
2821 ACCATATTCT TGGGAACAAG ATCTACAGCA TGGGGCAGAA TCTTTCCACC AGCAATCCTC
2881 TGGGATTCTT TCCCGACCAC CAGTTGGATC CAGCCTTCAG AGCAAACACC GCAAATCCAG
2941 ATTGGGACTT CAATCCCAAC AAGGACACCT GGCCAGACGC CAACAAGGTA GGAGCTGGAG
3001 CATTCGGGCT GGGTTTCACC CCACCGCACG GAGGCCTTTT GGGGTGGAGC CCTCAGGCTC
3061 AGGGCATACT ACAAACTTTG CCAGCAAATC CGCCTCCTGC CTCCACCAAT CGCCAGTCAG
3121 GAAGGCAGCC TACCCCGCTG TCTCCACCTT TGAGAAACAC TCATCCTCAG GCCATGCAGT
3181 GG
```

FIG. 2B

HEPADNAVIRUS CORES

The present application claims the right of priority to U.S. application Ser. No. 60/021,561, filed Jul. 11, 1996.

The present invention relates to cell-free hepadnavirus-derived core particles comprising hepadnavirus core proteins, hepadnavirus polymerase and a nucleic acid such as RNA that is a template for initiation, initial chain elongation or other steps in the replication of a nucleic acid strand encoding at least a portion of the viral genome.

Hepadnaviruses such as hepatitis B virus ("HBV") replicate by a unique pathway that has proved difficult to reconstitute in vitro. The viral genome is a partially duplex DNA. Covalently attached to the 5' end of the (−) strand is a copy of the viral-encoded polymerase enzyme (P) involved in viral replication. The (−) strand contains the entire viral genome. The ends of the (−) strand are not ligated, but instead are held in proximity to one another by an overlapping (+) strand which, depending on the viral isolate, comprises about 20% to about 80% of the length of the (−) strand. The (+) strand has a short, capped segment of RNA covalently attached at the 5' end. After infection, the viral genome is believed to migrate to the nucleus of the infected cell, where cellular DNA repair processes are believed to convert it to a closed, circular form, termed "cccDNA". The closed, circular form is then transcribed to create messenger RNA's encoding viral proteins, including the hepadnavirus polymerase and the hepadnavirus core protein (C) that forms the core particle (i.e., capsid) that encapsidates the viral genetic information (thereby becoming a nucleocapsid). Some of the RNA transcripts are full-length and serve as the template for the replication of the viral genome; these RNA transcripts are known as pregenomic RNA (pgRNA). Hepadnavirus polymerases function (a) as reverse transcriptases, synthesizing the (−) strand of the genomic DNA using the pgRNA as a template, (b) as DNA polymerases, synthesizing the (+) strand of genomic DNA, and (c) as RNase Hs, sequentially digesting portions of the pgRNA template immediately after they have been reverse transcribed. See, Ganem et al. Infectious Agents and Disease 3: 85093, 1994, for a review of the literature on hepadnavirus replication.

The pgRNA typically has the following properties: (a) it is capped; (b) it is greater than genome length; (c) each end (both the 5' and the 3' end) has a repeat that includes (i) a sequence element termed "DR1" whose 3' copy is the apparent replication origin of the virus and (ii) a stem-loop-bulge sequence element, termed "ε", that contains the true replication origin; and (d) just to the 5' side of the 3' repeat there is another copy of the replication origin sequence designated the "DR2" element. According to current understanding, in the cytoplasm the hepadnavirus polymerase and pgRNA are encapsidated into the core particle formed from multiple copies of C. Hepadnavirus polymerase interacts with the 5'ε element and reverse transcribes a 3 to 4 base oligomer from the template provided by a sequence within the bulge of the stem-loop-bulge sequence. The first covalent bond in this reverse transcription is formed between a tyrosine hydroxyl of hepadnavirus polymerase and the 5' phosphate of a deoxynucleotide specified as complementary to a nucleotide of the stem-loop bulge template (see step 1 illustrated in FIG. 1). Thus, in a sense, hepadnavirus polymerase is the "primer" for the initial reverse transcript. This initial bond formation and the subsequent formation of the initial three to four-mer is termed the "priming" reaction. The protein and covalently attached oligomer then migrate to a complementary sequence found in the 3' DR1 element. This migration step is termed the "translocation" reaction. From the three or four-mer now base-paired at the 3' DR1, the polymerase reverse transcribes through to the 5' end of the pgRNA (see step 2 illustrated in FIG. 1), thereby synthesizing the (−) strand of the viral genome. This reverse transcription step is here termed the "(−) strand elongation" reaction. Concurrently with catalyzing the reverse transcription, a separate domain of hepadnavirus polymerase exhibits a RNase H activity that digests the RNA after it has been reverse transcribed into DNA (see step 3 illustrated in FIG. 1). Upon completion of the synthesis of the (−) strand, a 17 to 18 base residue of the 5' end of the pgRNA including the DR1 sequence remains (see step 4 illustrated in FIG. 1). This residue is translocated to the complementary DR2 element of the (−) strand, and then serves as the primer for the synthesis, again mediated by hepadnavirus polymerase, of a (+) strand priming fragment of the (+) strand complementary to the 5' end of the (−) strand (see step 5 illustrated in FIG. 1). A portion of this (+) strand priming fragment is also complementary to the 3' end of the (−) strand and, through this complementarity, the (+) strand priming fragment is used to create a non-covalent bridge linking the two ends of the (−) strand (see step 6 illustrated in FIG. 1). Once the bridge is formed, further (+) strand synthesis proceeds.

In infected cells, hepadnavirus replication occurs inside the viral nucleocapsid. Moreover, genetic studies have implicated C as critical to the process of viral replication in vivo. Nassal, J. Virol. 66: 4107–4116, 1992; Schlicht et al., J. Virol. 63: 2995–3000, 1989; Yu and Summers, J. Virol. 65: 2511–2517, 1991. Nonetheless, it has proved possible, after substantial initial difficulty, to measure some initial replicative activity in vitro—outside of the core particles—using copies of hepadnavirus polymerase produced by a variety of molecular biology-based techniques. See, for example, Seifer and Standring, J. Virol. 67: 4513–4520; Tavis and Ganem, Proc. Natl. Acad. Sci. USA 90: 4107–4111, 1993; Lanford, J. Virol. 69: 4431–4439, 1995; Seeger, U.S. Pat. No. 5,334,525. However, given the importance of C and core particles to replication in vivo, it is clear that such systems do not faithfully reflect the authentic replication environment and are thus of only limited value as tools for identifying antiviral agents that disrupt viral replication. Furthermore, it is believed that these systems have only a limited capability to elongate minus-strand DNA chains, and that these systems at least in vitro have not been shown to elongate de novo chains of more than, for example, 200 nucleotides.

Others have transfected mammalian cells in "trans", meaning two separate expression vectors were used to express C and polymerase and thus create core particles. The cells were transfected with (a) an expression vector specifying a pgRNA which encodes hepadnavirus polymerase but has a frame-shift mutation making it deficient for the production of C and (b) an expression vector encoding C. See, for example, Bartenschlager et al., J. Virol. 64: 5324–5332, 1990 and Hirsch et al., Nature, 344: 552–555, 1990, both of which articles report mutational studies indicating that hepadnavirus polymerase is needed to correctly package the pgRNA into viral core particles. What this prior work has not done is isolate core particles that are "frozen" in an early stage of the replication process such that the core particles can be used in an in vitro assay that reproduces the intra-core particle environment in which the replication process occurs in vivo. The core particles of this prior work are also believed to have replicated more extensively and have completed much of there (−)-strand synthesis. These prior art core particles thus have reduced reverse transcriptase activity in vitro relative to core particles frozen in a early stage of replication. I What is needed for determining whether a test compound inhibits early genomic replication mediated by hepadnavirus polymerase is an in vitro system wherein hepadnavirus polymerase operates within the core particle, its natural operative environment, and wherein hepadnavirus polymerase operates from an early stage of the synthesis of genomic DNA through a substantial amount of chain elongation. This need is met by the present invention which provides large quantities of substantially pure viral core particles containing an active hepadnavirus polymerase and a template RNA.

Hepadnavirus capsids have been produced in the recombinant baculovirus/insect cell expression systems. See for example Hildith et al., *J. Gen. Virol.* 71: 2755–2759, 1990 and Lanford and Notvall, *Virology* 176: 222–233, 1990. Hepadnavirus capsids have also been produced from recombinant bacteria. See for example Birnbaum and Nassal, J. Virol. 64: 3319–3330, 1990. These systems, however, did not produce core particles containing all three functional components: (1) P; (2) C; and (3) a nucleic acid that serves as a template for useful measurements of an activity of hepadnavirus polymerase. The present invention further provides hapadnaviral core particles with these components, such as recombinant, insect-cell-derived core particles, core particles produced in cells contacted with a reverse transcriptase inhibitor, and core particles that are especially suitable for assays for (+)-strand synthesis.

SUMMARY OF THE INVENTION

In one embodiment, the core particles of the compositions of the invention are "frozen" in an early stage of the replication process that produces genomic DNA from pgRNA. This "frozen" state is indicated by several functional measurements, including:

(i) The isolated core particles incorporate added deoxynucleotides into long reverse transcripts (which are preferably DNA molecules linked to the hepadnavirus polymerase), such as reverse transcripts in excess of 400, 2,400 or even 3,000 nucleotides in length. (The longer reverse transcripts are dependent on the presence of a sufficiently long template RNA.)

(ii) Where the template RNA has an $\epsilon$ element and a DR1 element whose first three or four nucleotides (5' to 3') are the same as a stretch of three or four nucleotides in the bulge of the $\epsilon$ element, the isolated core particles incorporate added deoxynucleoside triphosphates into long reverse transcripts with apparent origins that align with these three or four nucleotides of the DR1 element.

(iii) The isolated core particles are competent to conduct an authentic priming reaction, which can be measured by measuring the selective incorporation of individual deoxynucleotides into short reverse transcripts in the manner predicted by the sequences of the correct initial, or priming, reverse transcripts. For instance, if the correct priming transcript has the sequence GAA, then when dGTP is added guanosine is selectively incorporated into a conjugate with hepadnavirus polymerase; when dATP is subsequently added it is selectively incorporated into a larger conjugate with hepadnavirus polymerase. Alternatively, the use of the priming template of a template RNA can be confirmed by a comparative mutational analysis. The bulge region of the $\epsilon$ element that defines the priming template can be mutated, which mutation will result in a change in the apparent origin of (−) strand synthesis.

(iv) The isolated core particles are "frozen" in comparison to cores derived via expressing hepadnavirus polymerase and the hepadnavirus core protein in cis (i.e., from a single pgRNA-like mRNA). A useful comparative standard are core particles formed in HepG2.2.15 cells. Such comparative cells appear to have completed HBV (−)-strand DNA synthesis in vivo and in vitro are relatively more active for (+)-strand synthesis than for (−)-strand synthesis. The (+)-strand synthesis is, for example, inhibited by inhibitors of DNA-dependent DNA polymerases such as actinomycin D.

The above functional tests of the frozen state can be conducted in the presence of an effective amount of an inhibitor of DNA polymerase activity (i.e., an activity yielding DNA synthesis from a DNA template), such as in the presence of Actinomycin D, thereby confirming that the activity is reverse transcriptase activity or DNA-dependent DNA polymerase activity. The isolated core particles frozen in an early stage of replication provide tools for assaying whether a biological agent affects (−)-strand synthesis or RNase H activity associated with (−)-strand synthesis.

In a second embodiment, the core particles need not be frozen in an early stage of replication, and provide tools for assaying whether a biological agent affects (+) strand synthesis.

Thus, the invention is directed to these isolated core particles, methods of making these isolated core particles, and to methods of using these isolated core particles to discover or further characterize antiviral agents, as set forth further below.

Preferably, in one embodiment, at least about 0.1% of the isolated core particles of the invention are capable of at least one of the reverse transcriptase activities recited in the paragraph immediately above, more preferably at least about 1%, still more preferably at least about 10%.

The core particle composition of the invention can be prepared with at least about 10-fold more cell-free reverse transcriptase activity, measured for example by the incorporation of labeled deoxynucleoside triphosphates into polymerase conjugates, than core particles isolated from HepG2.2.15 cells. The HepG2.2.15 cell line is among the most widely used constitutively HBV-producing cell lines available for hepadnavirus research. Preferably, the core particles of the invention are at least about 20-fold more active than HepG2.2.15 core particles, more preferably at least about 100-fold.

In a preferred embodiment of the invention, the core particles have at least about 6% of the RNA content of capsids obtained from recombinant bacteria according to the method of Zheng et al., J. Biol. Chem. 267: 9422–9429, 1992 (which document is incorporated herein by reference in its entirety), more preferably at least about 25% of the reference content, and still more preferably at least about 50%.

The invention provides a non-infectious, recombinant hepadnavirus core particle composition comprising isolated hepadnavirus core particles, template RNA encapsidated in the same core particles and hepadnavirus polymerase encapsidated in the same core particles, wherein, upon addition of deoxynucleoside triphosphates to the composition, the hepadnavirus polymerase incorporates deoxynucleotides into reverse transcripts of the template RNA beginning with the first deoxynucleotide of the reverse transcript or within about ten deoxynucleotides, preferably within about three nucleotides, more preferably within about two nucleotides, still more preferably within about one deoxynucleotide, of the first deoxynucleotide of the reverse transcript. Yet more preferably, the hepadnavirus polymerase incorporates deoxynucleotides into reverse transcripts of the template RNA beginning with the first deoxynucleotide of the reverse transcript. Preferably, the hepadnavirus polymerase of the composition, upon addition of deoxynucleoside triphosphates, incorporates deoxynucleotides into reverse transcripts of at least about 400 deoxynucleotides, more preferably at least about 2,400 deoxynucleotides, still more preferably at least about 3,000 deoxynucleotides.

Preferably, in one embodiment of the hepadnavirus core particle composition, the template RNA molecule does not comprise a sequence encoding both the hepadnavirus polymerase and the hepadnavirus C. In one embodiment, the template RNA molecule does not comprise more than one $\epsilon$ element. In another embodiment, the template RNA molecule encodes both hepadnavirus polymerase and hepadnavirus C.

Preferably, the hepadnavirus core particle composition, upon addition of deoxynucleoside triphosphates, incorporates deoxynucleotides into quantities of (+)strand DNA.

Preferably, the template RNA comprises (a) an RNA with an $\epsilon$ element with a priming template and (b) an acceptor site comprising the same sequence as the priming template, and the composition is such that, upon addition of deoxynucleoside triphosphates to the composition, the hepadnavirus polymerase incorporates deoxynucleotides into continuous reverse transcripts of the template RNA of at least about 400 nucleotides that have 5' ends that align with the acceptor site sequence.

Preferably, template RNA comprises an RNA with an $\epsilon$ element and the composition is such that two separate portions of the hepadnavirus core particle composition, upon the addition of (a) for a first portion, the deoxynucleoside triphosphate for the predicted initial deoxynucleotide of priming template transcript, or (b) for a second portion, the deoxynucleoside triphosphate for the predicted initial deoxynucleotide of the priming template transcript and the deoxynucleoside triphosphate for the predicted second distinct deoxynucleotide utilized in the priming template transcript, synthesize, respectively, a first adduct with the polymerase and a second, larger adduct with the polymerase, and wherein the quantity of both the first adduct and the second adduct is at least about two-fold greater than the quantity of polymerase adducts formed when one or both of the other two deoxynucleoside triphosphates are used.

For use in the bioactive agent screening aspect of the invention, the composition can comprise a candidate bioactive agent. This aspect of the invention comprises identifying bioactive agents that interrupt or inhibit hepadnavirus replication or characterizing the potency of antiviral agents in interrupting or inhibiting hepadnavirus replication by (a) adding one or more deoxynucleoside triphosphates to a core particle composition that contains a candidate bioactive agent and (b) detecting the formation of reverse transcripts or detecting the size of the reverse transcript. Preferably, the added deoxynucleoside triphosphates are labeled and the detecting step comprises determining the amount of label incorporated into reverse transcripts or determining the size of reverse transcripts having associated label. Preferably, the added deoxynucleoside triphosphates are labeled with a radioisotope, a chromophore or a fluorescent molecule, and the detecting step comprises detecting radioactivity, chromophore-created optical density or fluorescent molecule-created fluorescence incorporated into reverse transcripts. Preferably, the detecting step comprises separating core particles containing reverse transcripts from unincorporated deoxynucleosides by precipitating the core particles. The precipitation can be acid precipitation. The detecting step can comprise contacting the reverse transcripts with a protease to digest away any protein conjugated with the reverse transcripts.

The method can further comprise comparing the amount of reverse transcript to the amount formed when the method is replicated in all aspects except that the candidate bioactive agent is omitted. Preferably, the template RNA in the core particle composition comprises an $\epsilon$ element with a priming template, the method further comprising measuring the priming reaction by adding a subset of deoxynucleoside triphosphates that allows the addition one or more of the priming template-directed nucleotides. In another embodiment, the template RNA in the core particle composition comprises an $\epsilon$ element and a DR1 element, and the method further comprises measuring those continuous reverse transcripts that have 5' ends that begin with an apparent DR1-contained origin of replication.

The invention further provides a method of preparing a hepadnavirus core particle composition comprising (a) hepadnavirus core particles, (b) template nucleic acid encapsidated in core particles and (c) hepadnavirus polymerase encapsidated in core particles, wherein, upon addition of deoxynucleoside triphosphates to the composition, the hepadnavirus polymerase incorporates deoxynucleotides from the added deoxynucleosides into reverse transcripts of the template nucleic acid beginning with the first deoxynucleotide of the reverse transcript or beginning within about ten deoxynucleotides of the first deoxynucleotide of the reverse transcript, the method comprising (1) transfecting or infecting a cell with one or more nucleic acid vectors that (i) encode hepadnavirus polymerase and express hepadnavirus polymerase in the transfected or infected cell and (ii) encode hepadnavirus C and express hepadnavirus C in the transfected or infected cell, and (2) isolating (for instance by disrupting cells) to release said core particles formed from the expressed hepadnavirus C and hepadnavirus polymerase and the template nucleic acid, which template nucleic acid is derived from one of the nucleic acid vectors. Preferably, (a) the mRNA transcript from the hepadnavirus polymerase encoding sequence or the mRNA transcript from the hepadnavirus C encoding sequence is the template nucleic acid, (b) the template RNA comprises an $\epsilon$ element, and (c) the template RNA is encapsidated in the core particles that are isolated from the cells. In one embodiment, the transfected or infected cell is an insect cell and the vector is a baculovirus vector. In another embodiment, the transfected or infected cell is a mammalian cell and the vector is a mammalian expression vector. In yet another embodiment, the transfected or infected cell is an yeast cell and the vector is a yeast expression vector. In still another embodiment, the transfected or infected cell is an bacterial cell and the vector is an bacterial expression vector.

The method can further comprise separating the core particles from cellular components of differing sizes and densities by centrifugation. The method can comprise separating the core particles from cellular components of differing densities by density gradient centrifugation or, the method can comprise, digesting the cellular components with enzymes such as proteases or nucleases to which the core particles are resistant.

In one embodiment, the method comprises, or the method can comprise, digesting the cellular components with enzymes such as proteases or nucleases to which the core particles are resistant, growing the transfected or infected cell in the presence of a hepadnavirus polymerase-inhibiting effective amount of a reverse transcriptase inhibitor. In one embodiment, the hepadnavirus polymerase-encoding nucleic acid is on a first vector and hepadnavirus C-encoding nucleic acid is on a separate, second vector.

In certain embodiments the invention provides non-infectious, recombinant hepadnavirus core particle composition that is:

(a) isolated from cells transformed with one or more recombinant vectors encoding hepadnavirus core protein and hepadnavirus polymerase and contacted with a reverse-transcriptase inhibiting effective amount of a reverse transcriptase inhibitor; or (b) isolated from insect cells transformed with one or more recombinant baculoviruses encoding hepadnavirus core protein and hepadnavirus polymerase;

wherein the core particles comprise hepadnavirus polymerase and nucleic acid encapsidated therein such that, upon addition of deoxynucleoside triphosphates to the composition, the deoxynucleotides are incorporated into DNA. Preferably, a first recombinant vector encodes the core protein and a second vector encodes the polymerase. In one embodiment, the encapsulated nucleic acid includes RNA, and the addition of deoxynucleotides results in (−)-strand synthesis. In another embodiment, the addition of deoxynucleotides results in (+)-strand synthesis.

In other embodiments, the invention provides a non-infectious, recombinant hepadnavirus core particle composition comprising core particles that comprise hepadnavirus polymerase and nucleic acid encapsidated therein such that, upon addition of deoxynucleoside triphosphates to the composition, deoxynucleotides are incorporated into a substantial distribution of (+)-strand nucleic acids. A preparation of (+)-strand nucleic acids has a "substantial" distribution of nucleic acids if for example at least about 0.5% have size from about 0.1 to about 1.0 kb, preferably for about 0.1 to about 3.0 kb. More preferably, at least about 5% of the nucleic acids have molecular weights between about 0.1 and about 1.0 kb, and yet more preferably between 0.1 and about 3.0 kb. Still more preferably, at least about 50% of the nucleic acids have molecular weights between about 0.1 and about 1.0 kb, and yet more preferably between 0.1 and about 3.0 kb.

The core particles of any embodiment of the invention can be used in a method of identifying bioactive agents that interrupt or inhibit hepadnavirus replication or characterizing the potency of antiviral agents in interrupting or inhibiting hepadnavirus replication, the method comprising (1) adding one or more deoxynucleoside triphosphates to the core particle composition;

(2) adding a bioactive agent to the core particle composition; and (3) following steps (1) and (2), either (i) detecting formation of nucleic acids or detecting sizes of nucleic acids found in the core particle composition or (ii) measuring an RNase H activity exhibited by the core particle composition.

The invention is described with reference to three primary aspects: the core particle composition, the bioactive agent screening method and the production method. These are closely intertwined and it will be recognized that all preferred or alternate embodiments of the composition can be used in the screening method or produced by the production method, or that any preferred core particle recited with respect to the screening method or the production method is a part of the core particle composition aspect of the invention.

BRIEF DESCRIPTION OF THE DRAWINGS

FIGS. 2A and 2B show the sequence (SEQ ID NO:1) of an isolate of the ayw strain of human hepatitis B.

DEFINITIONS

Figure 1:
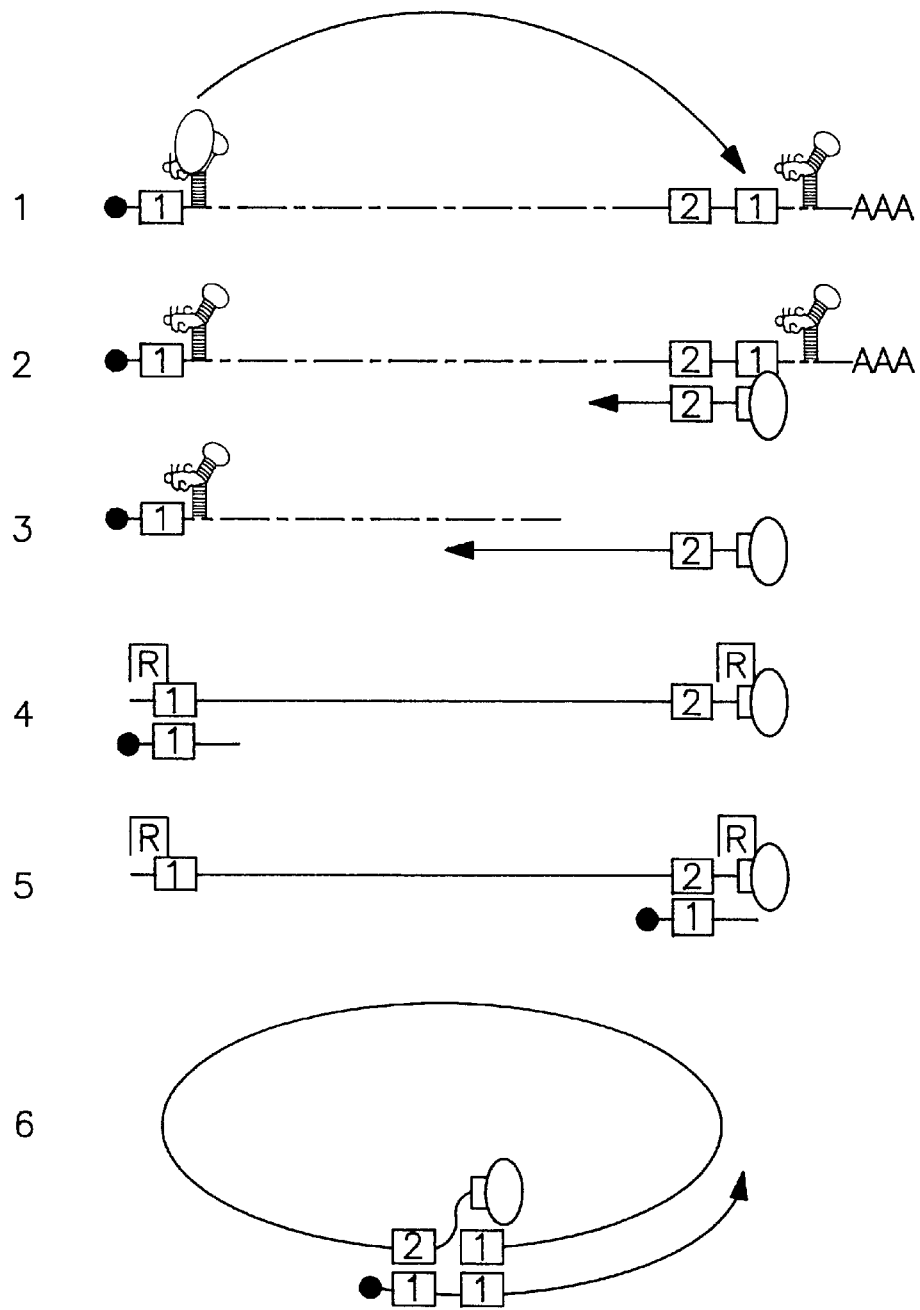
FIG. 1 illustrates the pathway of hepadnavirus genomic synthesis from pgRNA.
Figure 3:
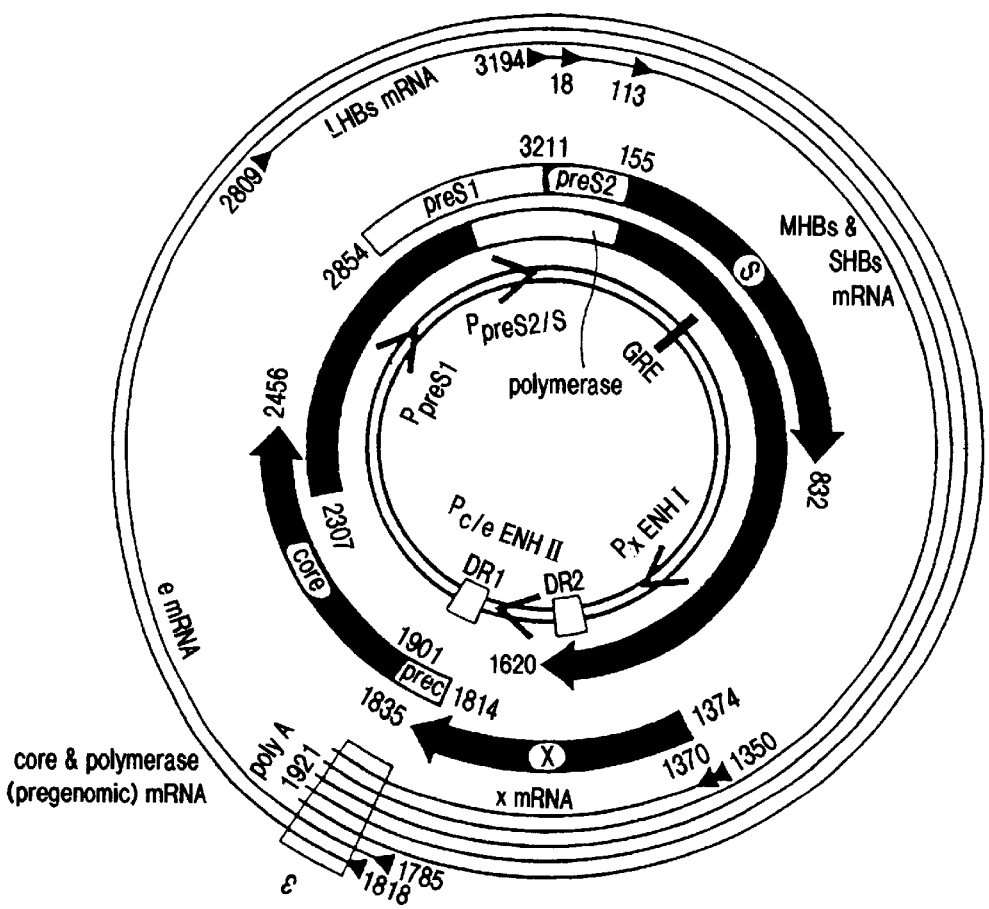
FIG. 3 shows a map of a hepatitis B isolate.

The following terms shall have the meaning set forth below:

Acceptor Site

An "acceptor site" is a sequence that is used as the site to which the polymerase translocates after the priming reaction. For any core particle composition, examinations of the apparent origins of reverse transcripts synthesized by the composition can be used to identify acceptor sites. For natural viral isolates, the predominantly utilized acceptor site is typically a sequence in the DR1 element that matches the sequence of the priming template.

Antiviral Agent

An antiviral agent is a bioactive agent that inhibits the reproduction or decreases the survival of a virus or inhibits the propagation of a virus. The inhibition includes without limitation replication, viral assembly or cellular infection, of a virus.

Apparent Origin of Replication

The common methodologies for determining the relative 5' placement of a polynucleotide against a complementary polynucleotide include primer extension methods and nuclease protection methods. In the context of this invention, when these methodologies are used to quantitate correctly initiated reverse transcripts, they do not necessarily identify whether the priming event occurred at the priming template; they only identify polynucleotides that appear to have 5' origins starting with a sequence aligned with, for instance, an acceptor site, which is believed to be a location to which polymerase translocates after an initial priming event. Thus, the phrase "apparent origin of replication" refers to the alignment of the 5' origin for hepadnavirus (−) strands against the corresponding (+) strand that is determined experimentally, regardless of whether in theory the "true" origin may be, and probably is, in the $\epsilon$ element.

Bioactive Agent

A bioactive agent is a substance such as a chemical that can act on a cell, virus, organ or organism, including but not limited to drugs (i.e. pharmaceuticals) to create a change in the functioning of the cell, virus, organ or organism. In a preferred embodiment of the invention, the method of identifying bioactive agents of the invention is applied to organic molecules having molecular weight of about 1500 or less.

Continuous Reverse Transcripts of the Template RNA

Continuous reverse transcripts of the template RNA are those that are a reverse transcribed, contiguous stretch of the template RNA without deletions or insertions.

Core Particles

A core particle is an enveloping shell of C protein, which can include nucleic acid and proteins encapsidated within the shell. Those core particles containing template RNA or DNA and polymerase are typically referred to as nucleocapsids. For hepadnaviruses, core particles mature to virions when they are encapsidated within a membranous shell, which membranous shell typically includes three hepadnavirus envelope proteins.

DR1 and DR2

The terms DR1 and DR2 refer to a sequence motif (see FIG. 2) typically found in three copies in hepadnavirus pre-genome RNA. By convention, the two copies located closest to the ends of the pgRNA are termed DR1 elements, and the third copy typically located near the 3' DR1 sequence motif, is termed the DR2 element. References to 5' or 3' orientation refer to the orientation of the (+) strand, unless otherwise specified. For each such sequence motif, both the sequence on the (+) strand and the complementary sequence on the (−) strand are referred to as either "DR1" or "DR2" elements. The 3' DR1 element serves as the apparent origin for the replication of the (−) strand. For the purposes of defining the invention, references to a DR1 element encompass elements that could be termed a DR2 element.

ε Element

"ε element" refers to a sequence motif typically found just 3' of a DR1 element, such as for example in the ayw strain of human hepatitis B beginning 13 nucleotides from the 3' end of the DR1 element. In the pgRNA, the sequence of each ε element has sufficient palindromic complementarity that it is expected to form, consistent with the widely accepted base pairing rules for RNA strands, a duplex structure having a terminal loop, a first stem portion having a helical, double-stranded structure, a bulge caused by a segment of RNA not having a complementary sequence, and a second stem portion, with the bulge located between the two stem portions. It is believed that the bulge functions as the template for the earliest (i.e., priming) polymerization steps of reverse transcription.

Hepadnavirus Polymerase Inhibiting Effective Amount

A hepadnavirus polymerase inhibiting effective amount of a reverse transcriptase inhibitor is an amount effective in the context of its use to reduce the amount of DNA synthesis occurring off of RNA templates. Typically, the inhibitor is added to cell cultures used to produce the core particles of the invention.

Minus (−) Strand/plus (+) Strand

The (−) strand is the nucleic acid strand complementary to the template RNA; (+) strands are template RNA or a DNA complementary to the (−) strand.

Non-infectious Core Particles

Core particles are non-infectious if they lack the genetic information needed to direct the synthesis of a hepadnavirus virion, which information is believed to include at least the intact pgRNA, the sequences for hepadnavirus C, hepadnavirus polymerase and at least a hepadnavirus envelope protein.

Priming Template

Typically, it is the 1st through the 3rd, or alternatively the −1 nucleotide through 3rd, nucleotides of the bulge of the ε element structure, reading 3' to 5', that are initially reverse transcribed by hepadnavirus polymerase, and it is this 3-mer or 4-mer that is referred to here as the "priming template." For a particular viral isolate, the start of the priming template can be inferred by primer extension analysis, such as that described by Lanford et al., J. Virol., 69: 4431–4439, 1995, which identifies the apparent origin of replication, or through experiments that isolate the priming reaction (see, e.g., Wang and Seeger, J. Virol. 67: 6507–6512, 1993).

Purified Isolated Core Particles

Compositions of core particles are purified if at least about 20% by weight of nonvolatile components of the composition are viral cores, and "isolated" if separated from other components of source cells.

RNase H

An endonuclease that excises ribonucleotides from the RNA strand of a DNA-RNA hybrid substrate.

Replication of a Method

Reference to replicating an assay method means conducting the assay either in parallel or at separate times using the same assay conditions.

Selectively Incorporate

Nucleotides from deoxynucleoside triphosphates are selectively incorporated into a protein conjugate or a nucleic acid sequence if at least about two-fold more of the nucleotide is incorporated than is any other nucleotide, which alternate incorporation can be tested in a parallel reaction.

SDS-PAGE

"SDS-PAGE" means polyacrylamide gel electrophoresis of proteins in the presence of sodium dodecyl sulfate.

DETAILED DESCRIPTION

As discussed above, it has been possible to assay substances for their effects on the hepadnavirus polymerase, P, but there is reason to believe that the actual physiological environment in which hepadnavirus polymerase functions, specifically the interior of the core particle, alters the enzymatic properties of hepadnavirus polymerase. Towards the goal of isolating hepadnavirus polymerase-containing core particles, the present applicants sought to recombinantly express hepadnavirus polymerase and C in the hopes of isolating core particles in which hepadnavirus polymerase activity could be detected. Unexpectedly, applicants have identified procedures that create such core particles in large quantities including useful quantities of template RNA that can be reversed transcribed in vitro from an early stage of the replication process. These core particles are referred to as "frozen" in an early stage of the replication process. These core particles can be prepared so that the template RNA contains both an ε element and a DR1 element with an acceptor site, in which case the reverse transcripts can be shown to correctly originate at the DR1 element.

The invention provides novel core particle compositions and methods of assaying for inhibitors of hepadnavirus replication, including inhibitors of one or more of the priming reaction, the translocation reaction, the (−) strand elongation reaction, the (+) strand elongation reaction, and the RNase H reaction.

Two features are believed to be independently important to the production of the "frozen" core particles of the invention. In one aspect, the use of vectors in trans that create template RNAs where necessarily the 3' regulatory elements (ε or DR1) are not on the same nucleic acid molecule with the 5' regulatory elements is believed to help produce useful core particles. In another aspect, the use of a reverse transcriptase inhibitor has been found to help produce useful core particles while surprisingly not destroying the functioning of the host cell or the vector used to transform the host. The combination of these two approaches also helps produce useful core particles.

The use of baculoviral expression systems is a preferred method of expressing hepadnavirus polymerase and C to create the core particle compositions of the invention. Techniques for growing suitable insect cells, for preparing baculovirus stocks, and generally for expressing proteins through this system are extensively described in Baculovirus Expression Vectors—A Laboratory Manual, Oxford Press, New York, 1994, Ausubel et al., Current Protocols in Molecular Biology, John Wiley & Sons, New York, as updated as of June, 1996, and in Ausubel et al., Short Protocols in Molecular Biology, John Wiley & Sons, New York, 1992. Other expression systems, including eukaryotic expression systems, such as mammalian expression systems, yeast expression systems and bacterial expression systems, can be used to prepare the core particle compositions of the invention. These kinds of expression systems are described in a number of texts including Ausubel et al., Current Protocols in Molecular Biology, John Wiley & Sons, New York, as updated as of June, 1996, Ausubel et al., Short Protocols in Molecular Biology, John Wiley & Sons, New York, 1992, and Sambrook et al., DNA Cloning, a Laboratory Manual, Cold Spring Harbor, 1989. These same text sources can generally be referenced to identify any methodology referred to herein without specific enumeration of now well-known method steps.

A suitable expression vector is capable of fostering expression of the included hepadnavirus polymerase or C-encoding DNA in a host cell, which can be eukaryotic, fungal, or prokaryotic. Suitable expression vectors include pRc/CMV (Invitrogen, San Diego, Calif.), pRc/RSV (Invitrogen), pcDNA3 (Invitrogen), Zap Express Vector (Stratagene Cloning Systems, LaJolla, Calif.); pBk/CMV or pBk-RSV vectors (Stratagene), Bluescript II SK +/-Phagemid Vectors (Stratagene), LacSwitch (Stratagene), pMAM and pMAM neo (Clontech, Palo Alto, Calif.), pKSV10 (Pharmacia, Piscataway, N.J.), among others. Useful yeast expression systems include, for example, pYEUra3 (Clontech). Useful baculovirus vectors include several viral vectors from Invitrogen (San Diego, Calif.) such as pVL1393, pVL1392, pBluBac2, pBluBacHis A, B or C, and pbacPAC6 (from Clontech). Preferred host cells are Spodoptera frugiperda (fall armyworm) cells, especially the Sf9 cells that are derived from fall armyworm pupal ovaries (ATCC accession no. CRL 1711) or the Sf21 cells that are also derived from fall armyworm and are the parent of Sf9 cells. For the present purposes references to "transfection" encompass "infection" when the process of inserting vector nucleic acid into a cell is an infective process.

In some instances it is desirable to further increase the RNA content found in core particles of the invention. Site-directed mutagenesis to ablate certain apparent phosphorylation sites in the core protein (Hatton et al., J. Virol. 66: 5232–5241, 1992; Lanford & Notvall, Virology 176: 222–233, 1990) (serine 155, threonine 160, serine 162, serine 168, serine 170, serine 176, serine 178 and serine 181, as numbered in the core protein sequence of Galibert et al., GenBank accession number J02203) can be conducted to help achieve such an increase. (As numbered for the C of the adw strain, the relevant residues are: serine 157, threonine 162, serine 164, serine 170, serine 172, serine 178, serine 180 and serine 183.)

The present invention extends beyond the particular nucleic acids or nucleic acid constructs identified herein and encompasses the preparation of non-infective, recombinant hepadnavirus core particles that are well suited for use in drug discovery programs aimed at identifying inhibitors of early replication processes mediated by hepadnavirus polymerase. As such, the particulars of the construct sequences are not believed to be needed to identify the invention. However, to facilitate understanding of the invention, the sequence of the hepatitis B ayw strain as set forth in Galibert et al., "Nucleotide sequence of the hepatitis B virus genome (subtype ayw) cloned in *E.coli*," Nature 281: 646–650, 1979, is set forth in FIG. 2 (SEQ ID No: 1). The DR1 and DR2 elements are indicated, as is the ε element. Those bases in the ε element that are in the first stem segment are indicated with an underlined "S"; the bulge bases are indicated with a "B"; the second stem bases are indicated with an "S" but no underlining; the loop bases are indicated with "L"; and "M" indicates a single base in the second stem section that has no base-pair partner. The underlined "TTC" sequence is the priming template which is believed to be the template for the initial (−) strand synthesis. With some frequency, the sequence "ATTC" is utilized as the priming template.

Sources of hepadnavirus nucleic acid sequences for use in constructing expression vectors in accordance with the present invention include plasmid pTHBV-1 (Christman et al., Proc. Natl. Acad. Sci. USA 79:1815–1819, 1982) and pHBV-1 (Hirschman et al., Proc. Natl. Acad. Sci. USA 77: 5507–5511, 1980), which were from George Acs of Mt. Sinai Medical Center, (New York, N.Y.). Plasmid THBV-1 contained a head-to-tail dimer of the complete HBV genome (subtype ayw), and plasmid HBV-1 contained a single EcoR I—EcoR I copy of the genome. Nucleotide numbering used herein is from the HBV ayw sequence (GenBank accession number J02203). Additional useful sources include plasmid pAM6, which is available from the American Type Culture Collection under Accession Nos. 45020, 39630 and 40101.

A number of other hepadnaviruses can be used in the invention, including mammalian viruses such as woodchuck and ground squirrel HBVs and avian hepadraviruses such as duck hepatitis B virus and heron hepatitis virus. Preferably, the polymerase of the composition of the invention is derived from human hepatitis B and the core particles comprise hepadnavirus C derived from human hepatitis B. It is believed, at least for mammalian hepadnaviruses that in most, if not all cases, the C protein from one hepadnavirus and polymerase from another hepadnavirus can be combined to form a core particle according to the invention. See, Ziermann and Ganem, Virology 219: 350–356, 1996.

Using the methodology described herein, expression vectors were constructed that (1) expressed mRNA for C, (2) expressed MRNA for the ε element fused to 5' end of the C sequence, (3) expressed mRNA for the DR1 and ε elements fused to 5' end of the C sequence, (4) expressed mRNA for the hepadnavirus polymerase sequence, and (5) expressed mRNA for the DR1 and ε elements fused to 3' end of the hepadnavirus polymerase sequence. The clone designations are as follows:

| Expression Vector Insert | Prokaryotic Expression Vector | Baculovirus Transfer Vector | Baculovirus |
|---|---|---|---|
| C | pRH203 | pRH205 | BV-C |
| ε-C | pRH216 | pRH217 | BV-EC |
| DR1-ε-C | pRH220 | pMS101 | BV-DEC |
| Polymerase | — | pRH213 | BV-P |
| Polymerase-DR1-ε | pRH209 or pRH210 | pRH212 | BV-PDE |
| C-Polymerase | — | pRH222 | BV-CP |
| C-Polymerase-DR1-ε | pRH218 | pRH223 | BV-CPE |
| ε-C-Polymerase | — | pRH224 | BV-ECP |
| ε-C-Polymerase DR1-ε | pRH219 | pRH225 | BV-ECPE |

The ε element and DR1 element in a given viral isolate typically share a sequence homolog corresponding to the priming template. For instance, in the HBV ayw sequence, these sequences are those underlined in the insert below. In the insert below, the bolded sequence represents the element sequence; adjacent sequence is shown for the 5' side of DR1.

DR1: (SEQ ID NO: 2): AACTTT<u>TTCAC</u>CTCTGC

ε: (SEQ ID NO: 3): TGTTCATGTCCTACTG TTCAAGCCTCCAAGCTGTGCCTTGGGTGGCTTTGG-GGCATGGACA

Oligonucleotide-directed mutagenesis was conducted to change the TTTCAC sequence associated with the DR1 element to GGGCCC, and to change the G<u>TTCAA</u> sequence of the ε element to GGGCCC. In this way, baculovirus transfer vectors were constructed to make the following baculoviruses, where * denotes the mutated ε element and DR1* denotes the mutated DR1 element.

| Expression Vector Insert | Baculovirus |
|---|---|
| ε*-C | BV-E*C |
| Polymerase-DR1-ε* | BV-PDE* |
| Polymerase-DR1*-ε | BV-PD*E |
| Polymerase-DR1*-ε* | BV-PD*E* |

Plasmid constructs encoding the HBV C gene of strain adw (Valenzuela et al., ICN-UCLA Symp. Mol. Cell. Biol. 18: 57–70, 1980) downstream of a SP64 in vitro transcription promoter (Standring et al., UCLA Symp. Mol. Cell. Biol. New Series 70:117–127, 1987; Zhou & Standring, J. Virol. 65:5457–5464, 1991) can be used for oligonucleotide-directed mutagenesis by the method of Kunkel (Proc. Natl. Acad. Sci. USA 82: 488–492, 1985) to ablate several apparent phosphorylation sites within the carboxyterminal RNA binding domain of hepadnaviral C by point mutation of serine or threonine encoding sequences to alanine encoding sequences. Plasmid DNAs used for the generation of the corresponding recombinant baculoviruses can be constructed by isolating the Hind III-BstEII fragments from appropriate pSP64 parent plasmids (the fragment encoding the C including the ser-to-ala mutations referred to as C*) and cloning into SmaI-digested pVL-1393 (a baculovirus transfer vector available from Invitrogen, San Diego, Calif.) using standard molecular cloning techniques as described for example in Sambrook et al., DNA Cloning, a Laboratory Manual, Cold Spring Harbor, 1989. These methods have been used to generate recombinant baculoviruses BV-DEC-S1, S2, S3 and BV-DEC-S1,S2,S4 containing a DR1 element, an epsilon element upstream of C and a series of ser-to-ala and thr-to-ala changes: serine 157, threonine 162, serine 164, serine 170, serine 172 in BV-DEC-S1,S2,S3 and serine 157, threonine 162, serine 164, serine 178, serine 180, serine 183 in BV-DEC-S1,S2,S4), respectively.

Assays examining the polymerase activity and apparent replication origins from in vitro replication using cores isolated with one of the C-expressing baculoviruses and one of the polymerase-expressing vectors described herein yield the following information.

1. Both the C-expressing or the polymerase-expressing vector are utilized to make template RNA that is packaged in the core particles, so long as the template has an ε element.
2. The presence of an ε element is important—though not essential—to obtaining in vitro replication activity, but the priming template within the ε element can be varied.
3. After the priming reaction, translocation to an acceptor site in the template RNA strongly predominates over continued reverse transcription of the sequence downstream of the priming template.
4. Priming and translocation predominantly occurs in cis, meaning that after the priming reaction the polymerase seeks an acceptor site on the same template molecule as the ε element used for priming.
5. In the absence of an acceptor in the DR1 element, the polymerase appears to scan for a homolog elsewhere in the template molecules to which it then translocates. Thus, if a DR1 element of one of the vectors is the above-described mutant form lacking the acceptor site, then translocation occurs predominantly at "cryptic" acceptor sites. These cryptic acceptor sites may be utilized to a minor extent in the wild-type virus. If the ε element of one of the vectors is the mutant form and that vector has a wild-type DR1 element, and if apparent priming is measured for the template RNA from that vector, then predominately the polymerase is translocated to acceptor sites outside the DR1 element. If both the ε element of one of the vectors is the mutant form and that vector also has a corresponding mutant DR1 element, then translocation predominantly occurs to the mutant "acceptor site" of the mutant DR1 element.
6. Priming and translocation in trans (i.e., between two template nucleic acids) has been detected for the expression system combination made from BV-EC and BV-PDE*, where priming occurred in trans at the wild-type ε element of the C-expressing vector and translocation was to the acceptor site of the DR1 element of the polymerase-expressing vector. This result suggests that at least some core particles created from two vectors contain template derived from both vectors.
7. The presence of both an ε element and a DR1 element on both vectors used in a trans infection protocol results in a 30–40% improvement in (−)-strand synthesis versus the situation where both vectors have only an ε element.

These studies indicate that the requirements that allow the ε element to function are quite flexible, and that DR1 elements are useful but not essential to an in vitro assay.

The use of a hepadnavirus polymerase inhibiting effective amount of a reverse transcriptase inhibitor during the growth of the cells that produce the core particles increases the quality of the resulting core particle composition, as measured in terms of, for example, the ability to incorporate in vitro added deoxynucleoside triphosphates into long transcripts, or the ability to incorporate in vitro added deoxynucleoside triphosphates into long transcripts having the correct origin. Preferably, the reverse transcriptase inhibitor is not added until at least about one hour after the cells have been infected, such as during the period of time between about 1 hour and about 12 hours, or between about 1 hour and about 24 hours, after the infection. Of course, in any particular variation of the methodology of the invention the optimal timing for the addition of the reverse transcriptase inhibitor can be simply determined by trying variations of the timing and assessing the quality of the resulting compositions using the methods described herein. Phosphonoformate (Foscamet, typically as the trisodium salt) is a preferred inhibitor.

The polymerase activity exhibited by core particles of the invention is active in the presence of concentrations of Actinomycin D, such as 100 µg/ml Actinomycin D, that are known to inhibit polymerase activity from a DNA template but not to inhibit reverse transcriptase activity from an RNA template. This observation further confirms that the primary activity observed is the (−) strand synthesis from an RNA template. Site-directed mutagenesis has been used to change an tyr-met-asp-asp (SEQ ID NO:16) sequence in the HBV polymerase active site to a tyr-met-his-ala (SEQ ID NO:17) sequence, a mutation that has been previously shown to destroy polymerase activity. See, for example, Seifer and Strandring, Intervirology 38:295–303,1995; Wang & Seeger, Cell 71:663–670, 1992. For an analogous active site mutation, see Radziwill et al., J. Virol. 64:613–620,1990. When this mutant is used in the methods of the invention to create core particles, the core particles lack polymerase activity. This observation confirms that it is indeed hepadnavirus polymerase activity that is being observed in the core particles of the invention.

When the invention has been practiced to prepare core particle compositions without the use of a hepadnavirus polymerase inhibiting effective amount of a reverse transcriptase inhibitor, better results have been obtained when the cells are transfected with the necessary expression vectors in "trans," meaning that the C-expressing sequence and the hepadnavirus polymerase-expressing sequence are located on separate vectors. While not wishing to be limited to a particular theory, it is believed that the use of infection in trans results in in vivo replication which is less efficient, allowing for the isolation of core particles frozen in an early stage of the replication.

Using the methods of the invention, quantities of core particles as high as 0.5 mg, preferably 1 mg, more preferably 2 mg, still more preferably 6 mg, per liter of suspension culture can be obtained.

Ordinarily, the assay for antiviral substances conducted with the core particle composition of the invention will be a straight-forward assay wherein a cocktail of suitable deoxynucleoside triphosphates and suitable salts and buffers is incubated with the core particles. Apparently, the core particles are sufficiently porous to allow the nucleoside triphosphates to migrate to the core particle interiors. Typically, the deoxynucleoside triphosphate element will include a deoxynucleoside triphosphate or a deoxynucleoside triphosphate analog that has a label, i.e., an easily measurable component, such as a radioisotope. A straight-forward way to quantitate the result is to separate nucleic acid, protein polymers or core particles from the nucleotide mono, di or tri-phosphates in the assay incubation, for instance by acid precipitation such as acid precipitation with trichloroacetic acid ("TCA"). The amount of label in the macromolecular precipitated fraction is representative of polymerase activity. Alternatively, for instance, the formation of higher molecular weight adducts of the hepadnavirus polymerase or of higher molecular weight nucleic acid polymers can be examined as a marker for polymerase activity. Typical salt additives include $MgCl_2$, $NH_4Cl$, or $MnCl_2$, at concentrations that can start with those typically used with polymerase reactions, but can be optimized or adjusted using the assay methods described herein. The assay will usually contain one or more stabilizing components such as a non-ionic detergent, bovine serum albumin (BSA) and tRNA, at concentrations that can start with those typically used with polymerase reactions, but can later be optimized or adjusted using the assay methods described herein. The pH of the reaction is typically about 7.4, but this value can be optimized or adjusted using the assay methods described herein. Antiviral activity determined for a substance with this assay can be compared to the substance's activity in inhibiting other polymerase or reverse transcriptase activities. Such a comparison assay using the HIV reverse transcriptase is described by Gu et al., Proc. Natl. Acad. Sci., USA 9: 2760–2764, 1995; an assay using the murine leukemia virus (MuLV) reverse transcriptase is described by Blain and Goff, J. Virol. 69: 4440–4452, 1995; and an assay using human DNA polymerase is described by Hart et al., Antimicrobial Agents and Chemotherapy 36: 1688–1694, 1992.

One method to identify the 5' end of a reverse transcript is primer extension, which is described in Calzone et al., Methods. in Enzymol. 152: 611–532, 1987 or in Loeb and Tian, J. Virol. 69: 6886–6891, 1995. A PCR-based improvement to the primer extension methodology is described in Nassal and Rieger, J. Virol. 70: 2764–2773, 1996. Another method is RNase protection, which is described in Friedberg et al., Archiv. Biochem. Biophys. 279: 167 et seq., 1990.

In vitro plus strand synthesis or minus strand synthesis in the core particles can be measured using hybridization techniques. For instance, the nucleic acid products from the in vitro reaction of the core particles with nucleoside triphosphates can be isolated, the protein component can be digested away, the nucleic acids can be separated by electrophoresis, the separated nucleic acids can be transferred to a membrane, and the membrane can be probed with appropriate (+) strand-specific probes.

To focus on (+)-strand synthesis, comparative reactions can be conducted in the presence of an inhibitor of DNA-directed DNA polymerase such as for example actinomycin D, so that (+)-strand synthesis is indicated by the inhibitor-sensitive activity.

The invention also relates to methods of measuring the effects of substances on the priming reaction. In one example, the priming transcript reverse transcribed from the ε element is GAA, which is extended after the translocation event to a sequence that begins with GAAAAAGTTGCAT (SEQ ID NO:4). In this example, dGTP alone can be incubated with the core particle composition, and the incorporation of guanosine monophosphate into a conjugate with the hepadnavirus polymerase is indicative of the priming reaction. Or, dGTP and dATP can be added, so that the incorporation of guanosine monophosphate and adenosine monophosphate into a conjugate with the hepadnavirus polymerase is indicative of the priming reaction and it is believed, of an initial portion of the continuation of reverse transcription that is believed to occur after translocation. These kinds of assays can be verified using SDS-PAGE to confirm that the conjugates are of appropriate size.

The activity of biological agents in affecting RNase H activity can also be measured. Such activity can be measured for example by incorporating labeled ribonucleotides into the RNA template of the core particles (for instance by growing the recombinant source cells in the presence of such ribonucleotides) and measuring release of the labeled ribonucleotides when the core particles are released from the frozen state by the addition of dNTPs. Alternatively, the activity from the cores of the invention can be measured free of the core particles, for instance using the method of Oberhaus and Newbold, J. Virol. 69: 5697–5704, 1995 (which document, and particularly the section on page 5698 under the heading "RNase H activity gel assay, is incorporated herein by reference in its entirety). The Oberhaus and Newbold method measures the extent to which the RNase H excises radiolabeled ribonucleotides from the RNA strand of a DNA-RNA hybrid substrate that is embedded into a gel. In the particular application described in the above-cited document, the RNase H enzyme is first denatured and electrophoretically separated from other proteins by SDS-PAGE in the DNA-RNA-substrate containing gel, the enzyme is renatured by extensive washing to dilute the SDS concentration, and, after an incubation period in an appropriatwe reaction buffer, the gel is again washed to allow the faster diffusion of digested ribonucleotides to elute from the gel.

Antibodies that can be used to quantitate the amount of core particles in a composition include rabbit polyclonal anti-HBc/e antiserum (DAKO Corp., Carpinteria, Calif.) and mouse monoclonal antibodies ("MAbs") against two capsid-specific epitopes HBc/α (MAb 3105) and HBc/β (MAb 3120)(M.Mayumi, JICHI Medical School, Tochigi-ken, Japan). Other quantitation methods will be apparent to those of ordinary skill, including electrophoresis with staining such as Coomassie blue staining, optical density measurements, Bradford assays, Lowry assays, and the like.

In an attempt to orient the reader and facilitate understanding of the invention, this specification describes the current understanding of the mechanism of hepadnavirus replication. However, of course, the applicants are not limited to any particular theory. For instance, according to theory, it is believed that priming occurs with the reverse transcription of the priming template, and this priming is followed by translocation to an acceptor site. However, the embodiment of the invention reciting the reverse transcripts originating at the apparent DR1-contained acceptor site does not incorporate the theory that, in fact, priming occurs at ε elements.

Particularly useful quantities of reverse transcripts of a template RNA are transcript amounts that, if the transcripts are labeled by radioactive nucleoside triphosphates during transcription, can be detected after electrophoretic separation by autoradiography with the aid of an enhancing screen for no more than about one day. A particularly useful purity for the core particle composition, which purity can be achieved with the present invention, is at least about 50% by weight of nonvolatile components of the composition are viral cores. Preferably, at least about 60%, more preferably at least about 75%, still more preferably at least about 85%, yet more preferably at least about 95%, of the nonvolatile components of such compositions are viral cores.

In purifying the core particles released from cells, the lysates can be treated with nucleases such as micrococcal nuclease and proteases such as proteinase K to destroy much of the non-core-particle material in the lysate. The cores, particularly their interiors, are resistant to protease and nuclease treatment. Pelleting through 25% sucrose is one way to isolate core particles. These core particles can be purified from baculoviruses by repeated resuspensions and relatively low speed centrifilgations that pellet the insoluble baculoviruses while leaving the core particles in suspension. Other useful purification steps can include, for example, further density-based centrifugation steps, ion exchange chromatography, hydrophobic interaction chromatography, hydroxyapatite chromatography and affinity chromatography such as antibody-based affinity chromatography.

As mentioned above, the core particles that can be isolated from HepG2.2.15 cells provides a useful reference that highlights the improved properties of the core particles of the present invention. The core particles of the invention are superior in terms of overall in vitro reverse transcriptase activity and in terms of the number of core particles that exhibit very early replication reactions. The use of a comparative reference sample is particularly useful since absolute quantitation of the properties of the core particles is difficult, though possible. HepG2.2.15 cells were derived from a well-established liver cell line, HepG-2, as described by Sells et al., Proc. Natl. Acad. Sci. USA 84: 1005–1009, 1987. The use of these cells is described in Korba and Milman, *Antiviral Research* 15: 217–228, 1991 and Jansen et al., Antimicrobial Agents and Chemotherapy 37: 441–447, 1993.

The following examples further illustrate the present invention, but of course, should not be construed as in any way limiting its scope.

EXAMPLE 1

Henadnavirus Polymerase and C-Encoding Constructs

Plasmid pTHBV-1 (Christman et al., *Proc. Natl. Acad. Sci. USA* 79:1815–1819, 1982) and pHBV-1 (Hirschman et al., *Proc. Natl. Acad. Sci. USA* 77: 5507–5511, 1980) were from George Acs of Mt Sinai Medical Center (New York, N.Y.). The gene for C was excised from pHBV-l as a Sty I fragment (nucleotides 1884–2459) and was blunt-ended by filling in with Klenow fragment. The blunt-ended fragment was cloned into the Sma I site of pBSII(SK+) (a "Bluescript" bacterial expression vector available from Stratagene, La Jolla, Calif.) creating plasmid pRH203.

An ε element was placed in front of a C-encoding sequence using PCR. Oligo RH 112 (CCCGAGCTCGGATCCTTGTTCATGTCCTACTGTTC, SEQ ID NO: 5) which contains Sac I and BamH I recognition sites and HBV sequences from 1847–1867, and oligo RH 113 (GCCTCGTCGTCTAACAACAG, SEQ ID NO: 6), which contains HBV sequences from 2361–2342, were used for PCR reactions with plasmid pTHBV-1. The PCR product was isolated by agarose gel electrophoresis and digested with Sac I and BspE I. This digested fragment was ligated into pRH203 (described above) that had been previously digested with Sac I and BspE I, resulting in plasmid pRH216.

Using this same protocol with a substitution of one of the PCR primers, both the DR1 and ε elements were placed in front of a C-encoding sequence to make plasmid pRH220. Oligo RH 111 (CCCGAGCTCGGATCCAACTTTTTCACCTC-TGCC, SEQ ID NO: 7), which contains Sac I and BamH I recognition sites and HBV sequences from 1820–1837, was used in place of oligo RH 112 in the above reactions. The longer amplification product produced with RH 111 and RH 113 contained both an ε element and a DR1 element.

To insure that the baculovirus system could not generate an infectious HBV particle, site directed mutagenesis was performed to introduce amber mutations in the surface protein ("S") open reading frame without affecting the hepadnavirus polymerase open reading frame. A 3.3 Kb fragment isolated from a partial Fsp I and partial Bgl II digest of pTHBV-1 and containing HBV sequences from 1804-3182/1-1986 was cloned into the EcoR V and BamH I sites of pBSII(SK+) to give plasmid pPE-T7. Site directed mutagenesis was performed by the method of Kunkel (*Proc. Natl. Acad. Sci. USA* 82: 488–492, 1985) using the following oligonucleotides for mutagenesis: RH 101 (GGATTCTTGTCTACTAGAAAAACCCCGCC, SEQ ID NO: 8) and RH 102 (CCAGAAGAACCTAC-TAGAAGATGAGGCATAGC, SEQ ID NO: 9). The alignment of these olignucleotides with the HBV genome is indicated in FIG. 2, where the mis-matched bases to be mutated are underlined. The DNA sequence changes directed by these oligonucleotides result in 4 amber stop codons in the surface protein open reading frame without creating amino acid changes in the Pol open reading frame. The mutant plasmid DNA was digested with Avr II and BsrG I which cut at positions 180 and 770 respectively. The 600 bp fragment was isolated and used to replace the corresponding wild type Avr II—BsrG I fragment in pPE-T7 to give plasmid pRH209. DNA sequencing confirmed that pRH209 contained only the desired mutations within the Avr II—BsrG I region. Plasmid RH209 harbors the sequences for the hepadnavirus polymerase and the DR1 and ε elements.

A BamH I site was placed in front of the hepadnavirus polymerase gene by digesting pRH209 with Sal I and BspE I and ligating in a fragment resulting from annealing the following two oligonucleotides: RH 107 (TCGACGGATCCATAATG-CCCCTATCCTATCAACACTT, SEQ ID NO: 10) and RH 108 (CCGGAAGTGTT-GATAGGATAGGGGCATTATGGATCCG, SEQ ID NO: 11). The annealed oligonucleotides have the proper overhangs for ligation to the Sal I and BspE I sites, and contain an internal BamH I site (G/GATCC) The resulting plasmid is pRH210.

Plasmid constructs encoding both C and hepadnavirus polymerase downstream of the same promoter were constructed by isolating the BspE I-Sac I fragment from pRH210 (the fragment encoding hepadnavirus polymerase and the DR1 and ε elements) and cloning into BspE I—Sac I digested pRH203 (encoding C) and BspE I—Sac I digested pRH216 (encoding C and an element) to give pRH218 and pRH219 respectively.

Plasmid DNAs used for the generation of recombinant baculoviruses were constructed by isolating the appropriate restriction fragments from the Bluescript vectors and cloning into pVL1393 (a baculovirus transfer vector available from Invitrogen, San Diego, Calif.). Plasmid pRH205 [which creates baculovirus BV-C] was constructed by moving the Sty I—Sty I fragment of pHBV1, blunt-ended, into the Sma I site of pVL1 393. Plasmid pMS 101 [which creates baculovirus BV-DEC] was constructed by moving the BamHI-EcoRI fragment from pRH220 into the BamHI-EcoRI site of pVL1393]. Plasmid pRH217 [which generates baculovirus BV-EC] containing the epsilon element and C was constructed by moving the BamH I-EcoR I fragment from pRH216 into the BamH I-EcoR I site of pVL1393. Plasmid pRH212 [which generates baculovirus BV-PDE] containing hepadnavirus polymerase and downstream sequences to nucleotide 1986, which downstream sequences include a DR1 element and an element, was constructed by partial BamH I digestion of pRH210 followed by digestion with Not I. The resulting 2.9 Kb BamH I—Not I fragment was isolated and cloned into the BamH I—Not I sites of pVL1393. Plasmid pRH213 [which generates baculovirus BV-P] containing hepadnavirus polymerase and downstream sequences to nucleotide 1804, which downstream sequences exclude the downstream DR1 element and an ε element, was constructed similarly to pRH212 except that Fsp I was used instead of Not I and the isolated fragment was cloned into the BamH I site and the EcoR I sites of pVL1393 that had been blunt ended by fill in with Klenow.

Constructs containing both C and hepadnavirus polymerase downstream of the same promoter were transferred in a similar manner to pVL1393 by partial BamH I digestion followed by either Not I or Fsp I digestion. Specifically, plasmid pRH223 [forming baculovirus BV-CPE], containing C, hepadnavirus polymerase, and the DR1 and ε elements, was constructed by partial BamH I digestion of pRH218 followed by digestion with Not I. The resulting 3.3 kb fragment was ligated into BamH I—Not I digested pVL1393. Plasmid pRH222 [forming baculovirus BV-CP], containing C and hepadnavirus polymerase, but excluding the DR1 and ε elements, was constructed by partial BamH I digestion of pRH218 followed by digestion with Fsp I. The resulting fragment was ligated into BamH I—EcoR I digested pVL1393, where the EcoR I site had been blunt-ended using the Klenow fragment. Plasmid pRH225 [forming baculovirus BV-ECPE], containing, in 5' to 3' order, an ε element, C, hepadnavirus polymerase, and DR1 and ε elements, was constructed by partial BamH I digestion of pRH219 followed by Not I digestion. The resulting fragment was ligated into BamH I—Not I digested pVL1393. Plasmid pRH224 [forming baculovirus BV-ECP], containing, in 5' to 3' order, an ε element, C and hepadnavirus polymerase, but excluding the DR1 and ε elements, was constructed by partial BamH I digestion of pRH219 followed by digestion with Fsp I. The resulting fragment was ligated into BamH I—EcoR I digested pVL1393, where the EcoR I site had been blunt-ended using the Klenow fragment.

EXAMPLE 2

Purification of HBV Core Particles from Insect Cells

Coinfection of Insect Cells:

For each preparation, a total of 3 L of SF9 cells (available from Invitrogen, San Diego, Calif.) were coinfected with a baculovirus preparation expressing hepadnavirus polymerase and a baculovirus preparation expressing C. In other experiments, SF21 cells (available from Invitrogen, San Diego, Calif.) were successfully used. Fifteen 500-ml erlenmeyer flasks containing $2 \times 10^8$ cells ($1 \times 10^6$/ml) in 200 ml of serum-free medium (Sf-900 SFM, GIBCO BRL, Gaithersburg, Md.) were each infected with 2 multiplicity of infection ("MOI") of BV-DEC a recombinant baculovirus expressing C (baculovirus BV-C can also be used) and with 6 MOI of BV-PE, a recombinant baculovirus expressing hepadnavirus polymerase. 1.5 mM trisodium phosphonoformate ("PFA," sold as Foscarnet Sodium by Sigma Chemical Co., St. Louis, Mo.) was added from 1 to 24 h later depending on the preparation, and the cells were incubated for a total of 3.5 days. In other preparations, PFA was omitted. The cells were harvested by low-speed centrifugation (2,000 rpm=900×g, 10 min, 4° C.) and the dry cell pellets were frozen in batches of 750 ml on dry ice and stored at −80° C.

Preparation of Lysates:

The frozen cell pellets were thawed at 37° C. The cells were lysed by resuspending them in 150 ml core lysis buffer (50 mM Tris-HCl pH 7.4, 150 mM NaCl, 10 mM EDTA, 0.75% NP-40) (1/20 of original volume) and keeping them on ice for 15 min. The lysate formed was clarified by low-speed centrifugation (3,000 rpm, 2,000×g, 4° C., 15 min), followed by centrifugation at 10,000×g at 4° C. for 20 minutes.

Limited Protease/Nuclease Treatment:

The clarified lysate was transferred into three 50 ml polypropylene conical tubes (e.g., available from Falcon Becton-Dickinson, Franklin Lakes, N.Y., or from Sigma Chemical Co., St. Louis). 50 μg/ml of Proteinase K (Boehringer Mannheim, Indianapolis, Ind., molecular biology grade) was added to each from a 15 mg/ml protease solution (stored at 4° C.). Then, $CaCl_2$ was added to make a 15 mM $CaCl_2$ solution and micrococcal nuclease (Pharmacia, Piscataway, N.J.; stored in aliquots at −20° C.) to make 8 units/ml of nuclease. The conical tubes were incubated at 37° C. for 15 min. The micrococcal nuclease activity was stopped by adding EDTA to increase the EDTA concentration by 5 mM (note: the buffer contained 10 mM EDTA without the addition). The lysates were again clarified by centrifugation at 10,000×g, as described above, and the supernates transferred to clean 50 ml polypropylene conical tubes.

Ultracentrifugation (Pelleting through 25% Sucrose):

Aliquots of 25 ml cleared lysate were layered on top of 11 ml of 25% (w/v) sucrose, 0.75% (v/v) Triton-X100 (which can be substituted with NP-40) in TNE (10 mM Tris pH 7.4, 1 mM EDTA, 150 mM NaCl) in Beckman SW28 Ultra Clear tubes (Beckman Instruments, Fullerton, Calif.). The tubes were centrifuged at 28,000 rpm, 141,000×g, for 15 h at 4° C. The supernatants were discarded, the pellets were washed once with 500 μl phosphate-buffered saline ("PBS," 137 mM NaCl, 2.7 mM KCl, 4.3 mM $Na_2HPO_4$, 1.4 mM $KH_2PO_4$, pH 7.3) and resuspended in 1/500 of original volume (=6 ml) of TNE. Pellets were brownish, and contained mainly baculovirus. The resuspended pellets were kept on ice for 10 to 15 min. The soluble core particles were separated from the insoluble baculovirus by centrifugation in an Eppendorf microcentrifuge (Brinkman Instruments, Westbury, N.Y.) for 5 min at 13,000 rpm, 10,000×g, and at room temperature. The resuspension and centrifugation steps were repeated for a total of 3 times. The purified HBV nucleocapsids were frozen on dry ice/ethanol in aliquots and stored at −80° C.

Analyses:

The core particles were quantitated by anti-HBc specific enzyme-linked immunosorbent assay ("ELISA"), essentially as described in Seifer and Standring, Virology 196: 70–78, 1993 and Seifer et al., J. Virol. 67: 249–257, 1993, and as detailed below.

Purity was assessed by SDS-PAGE on 15% or 18% gels with Coomassie blue staining. The core particles were electrophoresed on 1% native agarose gel to check for capsid integrity and contamination by free nucleic acids.

The activity of hepadnavirus polymerase in the isolated core particles was assessed as described in Example 4.

EXAMPLE 3

Further Core Particle Compositions

The methodology of Example 2 was used to create core particle compositions produced by the following baculovirus-infected cells. In vitro polymerase activity was determined using the method of Example 4. The apparent 5' origin of the in vitro-produced reverse transcripts were determined using the methodology of Example 7.

| $1^{ST}$ Baculovirus | $2^{ND}$ Baculovirus |
|---|---|
| BV-C | BV-P |
| BV-C | BV-PDE |
| BV-EC | BV-P |
| BV-EC | BV-PDE |
| BV-DEC | BV-P |
| BV-DEC | BV-PDE |
| BV-CP | NONE |
| BV-CPE | NONE |
| BV-ECP | NONE |
| BV-ECPE | NONE |

EXAMPLE 4

Assay for Reverse Transcript Synthesis

A 96 well plate was prepared with wells containing either various dilutions of test sample containing a prospective bioactive agent, a positive control, a known hepadnavirus polymerase inhibitor, or an EDTA sample for which no polymerase activity should be detected and which thus indicates, after the assay processing, non-specific, background radioactivity. The plate has eight rows of wells, A through H, and twelve columns of wells, 1 through 12. Test sample dilutions, 10 μl each in 4% DMSO, 96% 20 mM Tris-HCl, pH 7.4, are placed in the wells of columns 1 through 10. The wells of column 11 receive 10 μl each of 4% DMSO, 96% 20 mM Tris-HCl, pH 7.4. Wells A through D of column 12 receive 2 mM phosphonoformic acid (PFA), 10 μl each, in 4% DMSO, 96% 20 mM Tris-HCl, pH 7.4. Wells E through H of column 12 receive 50 mM EDTA, 10 μl each, in 4% DMSO, 96% 20 mM Tris-HCl, pH 7.4.

Each well received 10 μl of a reaction cocktail prepared as follows:

| Component | Volume (in μl) | Final Amount per Well |
|---|---|---|
| $H_2O$ | 581.9 | — |
| 1M $NH_4Cl$ | 165 | 75 mM |
| 1M Tris-HCl, pH 7.4 | 110 | 50 mM |
| 1M $MgCl_2$ | 44 | 20 mM |
| 10% Tween 20 | 22 | 0.1% |
| 10 mg/ml bovine serum albumin | 22 | 100 μg/ml |
| 10 mg/ml tRNA | 22 | 100 μg/ml |
| dATP, dCTP, dTTP; 10 μM each | 22 | 1 μM |
| core particle composition | 110 | 1 μg |
| [$_{33}$P] dGTP 10 mCi/ml, 2000 Ci/mmol | 1.1 | 0.1 μCi, 2.5 nM |

The 96-well plate was incubated at 37° C. for 3 hours, at which point 20 μl of 20% trichloroacetic acid (TCA), 2% sodium pyrophosphate was added. The plate was chilled to 4° C. and incubated for 15 minutes. The TCA precipitates were collected on a glass fiber filter plate (GF/B filters, Packard, Meriden, Conn.) pre-wetted with 0.1 M sodium pyrophosphate. The filters were washed 1 5× with water, followed 3× washes with ethanol. After air drying for 15 minutes, 30 μl of Microscint O scintillation fluid (Packard, Meriden, Conn.) was added to each of the filters, and radioactivity was detected using a Packard Topcount Liquid Scintillation Counter.

The background radioactivity determined from column 12, wells E through H, was subtracted from all of the remaining values. The data from experimental wells was compared to the data from the positive controls (column 11).

EXAMPLE 5

Additional Baculovirus Constructs

Vectors for constructing the baculoviruses E*C, PDE*, PD*E and PD*E* were prepared using a MORPH site-directed oligonucleotide mutagenesis kit according to the instructions supplied by the manufacturer (Sprime 3prime, Inc., Boulder, Colo.). The following oligonucleotide was used to create the mutation in the ε element:

MS30 (SEQ ID NO: 12): 5'-ATGTCCTACTG<u>GGC</u> <u>CC</u>GCCTCCAAGCTG

The following oligonucleotide was used to create the mutation in the DR1 element:

MS29 (SEQ ID NO: 13): 5'-ACCATGCAACTT<u>GGGC</u> <u>C</u>CCTCTGCCTAATC

EXAMPLE 6

Additional Core Particle Compositions

The methodology of Example 2 was used to create core particle compositions produced by the following baculovirus-infected cells. In vitro polymerase activity was determined using the method of Example 4. The apparent 5' origin of the in vitro-produced reverse transcripts were determined using the methodology of Example 7.

| 1ST Baculovirus | 2ND Baculovirus |
|---|---|
| BV-C | BV-PDE* |
| BV-C | BV-PD*E |
| BV-C | BV-PD*E* |
| BV-EC | BV-PDE* |
| BV-EC | BV-PD*E* |
| BV-E*C | BV-P |
| BV-E*C | BV-PDE |
| BV-E*C | BV-PDE* |
| BV-E*C | BV-PD*E |
| BV-E*C | BV-PD*E* |
| BV-DEC | BV-PD*E |
| BV-DEC | BV-PD*E* |

EXAMPLE 7A

Start Site Mapping by Primer Extension

Cells

Two types of cells were examined. First, insect cells infected with the expression vectors of the invention. 50 mls of insect cells were infected with the expression vectors of the invention and grown as described above in Example 2. The cells were collected at 700×g and washed with PBS. The cells were lysed by adding 5 ml of 50 mM Tris-HCl, pH 7.4, 150 mM NaCl, 10 mM EDTA, 0.75% NP-40 [nonylphenoxy polyethoxy ethanol, a non-ionic detergent available from several sources including Sigma Chemical, St. Louis, Mo.] and placing them on ice for 15 minutes. The lysate was clarified by centrifugation at 3,000 rpm, 2,000×g at 4° C. for 10 minutes.

Second, constitutively HBV infected HepG2.2.15 cells were grown to confluence on 24-well plates, resulting in 1–2×10⁶ cells per well. The cells were obtained from George Acs of Mt. Sinai Medical Center, (New York, N.Y.). The cells were washed 3× with PBS. To each well, 1 ml of lysis buffer (50 mM Tris-HCl, pH 7.4, 150 mM NaCl, 5 mM MgCl$_2$, 0.2% NP-40) was added and the wells incubated on ice for between 0.5 and 4 hours. The cellular lysate was harvested by repeatedly pipetting up and down, and the lysate was clarified by centrifugation for 5 minutes at 13,000 rpm in an Eppendorf microcentrifuge.

Preparation of Antibody-Sepharose Complex 70 mg of Protein A Sepharose Cl-4B powder (Pharmacia, Piscataway, N.J.) was added to 1 ml of PBS. The gel was washed 3× with 1 ml of PBS (should give 300 μl of packed gel sufficient for 25 to 30 immunoprecipitations). The gel was collected by centrifugation at low speed (1 min, 1,000 rpm, microcentrifuge). The gel was resuspended in 1 ml of lysis buffer and either (a) 20–40 μl of polyclonal anti-HBe/c antibody (rabbit, DaKo) or (b) 7–10 μl of rabbit-pot 1–832 antiserum (from Robert Lanford, South West Foundation, San Antonio, Tex.) was added. The resulting suspension was incubated for 6–14 h, depending on the preparation, on tilt shaker at 4° C. The gel was washed to remove unbound antibody with 3 washes with PBS (1 ml each) and collected by centrifugation as described above. The antibody-coupled beads in the gel were diluted 10-fold with 2.7 ml of lysis buffer (for α-core beads) or RIP dilution buffer (for α-pol beads). RIP dilution buffer is 50 mM Tris-HCl, pH 74., 190 mM NaCl, 6 mM EDTA, 1.25% Triton-X 100.

Immunoprecipitation

To 1 ml aliquots of clarified lysate add 200 μl of -HBc/ protein A sepharose (equals 20 μl of gel). Note: when using HepG2.2.15 lysates and lysis buffer, add 70 μl of 10% NP-40 (final NP-40 concentration should be 0.75–0.8%). Each such mixture is a "reaction." Incubate the mixtures for 8 to 14 h at 4° C. on tilt shaker, and thereafter rinse (and equilibrate) the beads 2× with 1 ml of EPA wash buffer (50 mM Tris-HCl, pH 7.4, 75 mM NH$_4$Cl, 1 mM EDTA). The beads are then collected by centrifugation, taking care to remove the buffer without disturbing the pelleted beads.

Endogenous Polymerase Assay (EPA)

The beads were resuspended in 50 μl EPA reaction mix (50 mM Tris-HCl, pH 7.4, 75 mM NH$_4$Cl, 1 mM EDTA, 20 mM MgCl$_2$, 0.1 mM β-mercaptoethanol, 0.5% Tween 20, 50 μM dNTP mix (Ultrapure, Pharmacia, Uppsala, Sweden)), and the resulting suspension was incubated at 37° C. for 6 h.

The beads were washed once with 800 μl IP wash buffer (50 mM Tris-HCl, pH 7.4, 150 mM NaCl, 5 mM EDTA, 1% Triton-X 100, 0.02% SDS) and resuspended in 50 μl TNE (10 mM Tris-HCl, pH 7.4, 150 mM NaCl, 1 mM EDTA) containing 1% SDS and 10 mM dithiothreitol. The beads were then heated to boiling temperature (100 C) for 7 min to disintegrate the capsids, and the supernates isolated by centrifugation and transferred to microfuge cups, with the supemates from 2.5 parallel reactions combined in each microfuge cup. RIP dilution buffer (50 mM Tris HCl pH 7.4, 190 mM NaCl, 6 mM EDTA, 1.25% Triton-X 100), containing 1 mM benzamidine, was added to each cup to make 1 ml. To each cup, 150 μl pol 1-832 coupled Protein A Sepharose (freshly prepared as described above) was added. Polymerase/DNA complexes were reacted with the derivatized Sepharose overnight at 4° C., on a tilt shaker. The beads were washed once with 1 ml IP wash buffer and once with 1 ml PBS, and then resuspended in 60 μl× Proteinase K cocktail (100 mM Tris HCl, pH 7.6, 150 mM NaCl, 12.5 mM EDTA, 1% SDS, 1 mg/ml Proteinase K). The bead-proteinase K suspensions were incubated for 60 min at 37 C, extracted 2× with phenol:chloroform:isoamyl alcohol (25:24:1), and the upper phases transferred to new microfuge cups. To each cup was added a 1/10th volume of 3 M sodium acetate, pH 5.2, 5 1100 ng/l tRNA, and 3 volumes of ethanol. The cups were kept on dry ice for 1 h, after which the precipitated nucleic acid was collected by centrifugation (13,000 rpm in a Eppendorf microfuge, 4° C., 25 min). The pellets were washed with 70% ethanol and re-pelletted by centrifugation. After air drying, the pellets were dissolved in 5.7 1H$_2$O.

Primers

The primers used were:

A: 5'-TTTACTGTTTTCGTAACAGTTTTG SEQ ID NO: 14, corresponding with nucleotides 4049 to 4072 of the pVL1393 transfer vector, 62 nucleotides upstream of the BamH I cloning site (on the same strand as the (+) strand HBV insert).

B: 5'-AGGTCTTTGTACTAGGAGGC SEQ ID NO: 15, corresponding with nucleotides 1764 to 1783 of the HBV ayw sequence.

C: 5'-GCTAGGCTGTGCTGCCAACT SEQ ID NO: 16, corresponding with nucleotides 1482 to 1401 of the HBV ayw sequence.

Primer A identifies extended products that apparently originate in the C ORF and extend into adjacent baculovirus sequences. Primer B identifies extended products that apparently originate toward the 3' end of the polymerase ORF at or close to DR1. Primer C identifies products that can extend as far as 446 nucleotides from DR1. Primers were labeled with $^{32}$P using $^{32}$P-ATP (NEN-DuPont, Boston, Mass.) and T4 polynucleotide kinase (New England Biolabs, Beverly, Mass.) as is described, for example, on page 4–22 of Ausubel et al., Short Protocols in Molecular Biology.

PCR-based Primer Extension Anaylsis

To each tube of isolated nucleic acids add 1.5 μl of one of the $^{32}$P-labeled primers (1.5–2×10$^6$ cpm), 1.0 μl 10× Vent DNA Polymerase buffer (New England Biolabs, Beverly, Mass.), 0.3 μl 100 mM MgSO$_4$, and 1.0 μl 2 mM dNTP. The tubes were heated to boiling for 2 min, and then chilled on ice. 0.5 μl Vent (exo-) DNA polymerase (2 U/μl; New England Biolabs) was added to each tube, and the solutions in the tubes were overlaid with 15 μl light mineral oil. The tubes were spun briefly to assure the aqueous contents were beneath the overlaid oil, after which the following temperature cycling rotocol was conducted:

| | |
|---|---|
| Preliminary heating: | 5 min at 94° C. |
| Cycling (30 x): | 30 sec at 95° C. |
| | 30 sec at 50° C. |
| | 30 sec at 72° C. |
| Wind-up: | 5 min at 72° C. |
| Stop: | at 4° C. |

4 1 of USB sequenase stop buffer (U.S. Biochemicals, Cleveland, Ohio) was added to each tube, mixed, and the tubes stored at −20° C. for later analysis.

The samples were analyzed by heating them at boiling temperature for 5 min, and loading them onto a 6% or 8% urea-containing sequencing gel as described, for example, in Section 7.6 of Ausubel et al., Short Protocols in Molecular Biology. The same primers were used to create an $^{35}$S-sequencing ladder, created as described in the manual for the sequencing kit from U. S. Biochemicals, which was used to align the extended primers created in the assay. (See, for example, Unit 7 of Ausubel et al., Short Protocols in Molecular Biology for methods of creating sequencing ladders.)

EXAMPLE 7B

Endogenous Polymerase Assay (EPA) for (+)-Strand Synthesis

The synthesis that is actinomycin D sensitive is measured with the above-described EPA assay where 80–100 μg per ml of actinomycin D are added in a comparative sample.

EXAMPLE 7C

Size Analysis of Endogenously Labeled DNA from Nucleocpsids

SF9 cells were harvested 90 hours postinfection with recombinant viruses (a) BV-ECPE, (b) BV-EC+BV-PDE, (c) BV-EC and (d) BV-PDE. For sample (e), intracellular core particles from HepG2.2.15 cells were collected after 10 days in culture. Immunoprecipitated core particles were subjected to EPA as described above, and deproteinized nucleic acids isolated from the assay samples were analyzed on a 1% agarose gel, and visualized by autoradiography. The ECPE cores (the "cis" cores) produce products ranging in size from 0.1 to 3.0 kb, with the majority being from 01 to 1.0 kb. The "trans" cores of sample (b) produced a similar pattern of product nucleic acids. However, the cis products but not the trans products were mostly actinomycin D sensitive. The HepG2.2.15 cells produced three fairly focused bands of 3.2 kb or greater.

EXAMPLE 8

Assay for Partial Reverse Transcripts Synthesized in the Presence of Ones, Two and Three Deoxyribonucleosides Triphosphates Core particle compositions, each from a 10 ml coinfection, were prepared using the immunoprecipitation methodology of Example 7. Sufficient core particle compositions were prepared to examine conjugate formation in the presence of the following deoxynucleoside triphosphate combinations:

(a) $^{32}$P-dGTP (b) $^{32}$P-dGTP, dATP (c) $^{32}$P-dGTP, dATP, dTTP (d) $^{32}$P-dGTP, dATP, dTTP, dCTP (e) $^{32}$P-dGTP, dATP, dTTP, dCTP, 1.5 mM PFA (f) $^{32}$P-dTTP (g) $^{32}$P-dTTP, dGTP (h) $^{32}$P-dTTP, dGTP, dATP (i) $^{32}$P-dTTP, dGTP, dATP, dCTP (j) $^{32}$P-dTTP, dGTP, dATP, dCTP, 1.5 mM PFA

The core particle compositions were suspended in 50 mM Tris-HCl, pH 7.4, 75 mM NH$_4$Cl, 1 mM EDTA, 20 mM MgCl$_2$, 0.1 mM β-mercaptoethanol, 0.5% Tween 20, 100 μM appropriate unlabeled dNTP (Ultrapure, Pharmacia, Uppsala, Sweden), 66 nM 32P-dGTP or $^{32}$P-dTTP (NEN-DuPont, Boston, Mass.) and incubated for 6 h at 37° C.

The beads were washed twice with 1 ml IP wash buffer and resuspended in 50 μl TNE containing 1% SDS and 10 mM dithiothreitol. The beads were then heated to boiling temperature (100 C) for 7 min to disintegrate the capsids, and the supernates were isolated by centrifugation and transferred to microfuge tubes. 500 μl RIP dilution buffer was added to each tube, and 150 μl pol 1-832 coupled Protein A Sepharose (freshly prepared as described in Example 7) was added. Polymerase/DNA complexes were reacted with the derivatized Sepharose overnight at 4° C., on a tilt shaker. The beads were washed once with 1 ml IP wash buffer, resuspended in 16 μl 1.5×SDS-PAGE loading buffer (see, Ausubel et al., *Current Protocols in Molecular Biology*), and heated to boiling for 5 minutes. The samples were analyzed by SDS-PAGE, gel bands were detected by exposing an X-ray film, and quantitation was with Phosphorimager (Molecular Dynamics, Synnyvale, Calif.).

EXAMPLE 9

Quantitation of Core Particles—ELISA Methodology 96 well Immulon 2 immunoplates (Dynatech, Alexandria, Va.) were coated overnight at 4° C. with (a) 500 ng per well mouse monoclonal anti-HBc/3120 (from M. Mayumi, JICHI Medical School, Tochigi-Ken, Japan) immunoglobulin G in 50 mM sodium carbonate buffer (pH 9.6) or (b) 5 g per well of polyclonal sheep immunoglobulin G anti-HBV C (generated by R. Thomssen and W. H. Gerlich, University of Göttingen, Göttingen, Germany). After three washes with PBS-0.1% (vol/vol) Tween 20, the plates were blocked with 10% (vol/vol) newborn calf serum (GIBCO BRL, Gaitherburg, Md.), TNE (50 mM Tris-HCl, pH 7.5, 100 mM NaCl, 1 mM EDTA) for 1 h at room temperature, and again washed three times with PB S-0.1% (vol/vol) Tween 20. The plates were then incubated for 2 h at 37° C. with control fluid or various dilutions of core particle compositions or with standards derived from *E. coli* core particles (from Chiron Corp., Emeryville, Calif.). All sample volumes were adjusted to 100 l with 1% (wt/vol) bovine serum albumin in PBS. After six washes with PBS-0.1% (vol/vol) Tween 20 and addition of 100 l of diluted rabbit anti-c/e serum (1/2,000 in 10% newborn calf serum-TNE; Dako Corp., Carpinteria, Calif.) the plates were incubated for a further 1 h at 37° C. After being washed, the plates were incubated for 1 h at 37° C. with a 1/5,000 dilution of horseradish peroxidase-coupled anti-rabbit immunoglobulin G (Organon Teknika, Durham, N.C.) in 10% newborn calf serum-TNE and washed six times with PBS-0.1% (vol/vol) Tween 20. Color development was initiated by adding 1 mg of o-phenylenediamine (Zymed, South San Francisco, Calif.) per ml and 0.0125% $H_2O_2$ in 22 mM citric acid-50 mM sodium phosphate (pH 5.1). $A_{490}$ was measured with a microplate reader (Thermomax; Molecular Devices Corporation, Sunnyvale, Calif.).

The nucleic acid or amino acid sequences referred to herein by SEQ ID NOs: are as follows:

What is claimed:

1. A non-infectious, recombinant hepadnavirus core particle composition comprising
   isolated hepadnavirus core particles,
   template nucleic acid encapsidated in said core particles and
   hepadnavirus polymerase encapsidated in said core particles,
   wherein, upon addition of deoxynucleoside triphosphates to the composition, the hepadnavirus polymerase incorporates deoxynucleotides into reverse transcripts of the template nucleic acid beginning with the first deoxynucleotide of the reverse transcript or within about ten deoxynucleotides of the first deoxynucleotide of the reverse transcript.

2. The composition of claim 1, wherein upon addition of deoxynucleoside triphosphates to the composition, the hepadnavirus polymerase incorporates deoxynudeotides into reverse transcripts of at least about 400 deoxynudeotides.

3. The composition of claim 1, wherein said template nucleic acid molecule does not comprise a sequence encoding both the hepadnavirus polymerase and the hepadnavirus core protein.

4. The composition of claim 3, wherein said template nucleic acid molecule does not comprise more than one ε element.

5. The composition of claim 1, wherein said template nucleic acid molecule encodes both hepadnavirus polymerase and hepadnavirus core protein.

6. The composition of claim 1, wherein, upon addition of deoxynucleoside triphosphates, the hepadnavirus polymerase incorporates deoxynucleotides into quantities of (+) strand DNA.

7. The composition of claim 1, wherein the polymerase is derived from human hepatitis B and the core particles comprise hepadnavirus core protein derived from human hepatitis B.

8. A method of identifying bioactive agents that interrupt or inhibit hepadnavirus replication or characterizing the potency of antiviral agents in interrupting or inhibiting hepadnavirus replication, the method comprising
   (a) adding one or more deoxynucleoside triphosphates to the core particle composition of claim 1;
   (b) adding a bioactive agent to the core particle composition; and
   (c) following steps (a) and (b), either (i) detecting formation of nucleic acids or detecting sizes of nucleic acids found in the core particle composition or (ii) measuring an RNase H activity exhibited by the core particle composition.

9. The method of claim 8, further comprising (c) (iii) or measuring the priming reaction.

10. A method of preparing a non-infectious, recombinant hepadnavirus core particle composition comprising (a) hepadnavirus core particles, (b) template nucleic acid encapsidated in core particles and (c) hepadnavirus polymerase encapsidated in core particles, wherein, upon addition of deoxynudeoside triphosphates to the composition, the hepadnavirus polymerase incorporates deoxynucleotides into reverse transcripts of the template nucleic acid beginning with the first deoxynucleotide of the reverse transcript or within about ten deoxynucleotides of the first deoxynucleotide of the reverse transcript, the method comprising
   transfecting or infecting a cell with one or more nucleic acid vectors that (i) encode hepadnavirus polymerase and express hepadnavirus polymerase in the transfected or infected cell and (i) encode hepadnavirus core protein and express hepadnavirus protein in the transfected or infected cell, and (iii) contain template nucleic acid,
   isolating said core particles formed from the expressed hepadnavirus core protein and hepadnavirus polymerase and the template nucleic acid, which is derived from one of the nucleic acid vectors.

11. The method of claim 10, further comprising growing the transfected cell in the presence of a hepadnavirus polymerase-inhibiting effective amount of a reverse transcriptase inhibitor.

12. The method of claim 10, wherein the hepadnavirus polymerase-encoding nucleic acid is on a first vector and hepadnavirus core protein-encoding nucleic acid is on a separate, second vector.

13. A non-infectious, recombinant hepadnavirus core particle composition isolated from cells, wherein said cells are transformed with one or more recombinant vectors encoding hepadnavirus core protein and hepadnavirus polymerase and contacted with a reverse-transcriptase inhibiting effective amount of a reverse transcriptase inhibitor, and wherein the core particles comprise hepadnavirus polymerase and template nucleic acid encapsidated therein such that, upon addition of deoxynucleoside triphosphates to the composition, the deoxynucleotides are incorporated into DNA.

14. The composition of claim 13, wherein a first recombinant vector encodes the core protein and a second vector encodes the polymerase.

15. The composition of claim 13, wherein the encapsulated nucleic acid includes RNA, and wherein the addition of deoxynucleotides results in (−)-strand synthesis.

16. The composition of claim 13, wherein the addition of deoxynucleotides results in (+)-strand synthesis.

17. A method of identifying bioactive agents that interrupt or inhibit hepadnavirus replication or characterizing the potency of antiviral agents in interrupting or inhibiting hepadnavirus replication, the method comprising (a) adding one or more deoxynucleoside triphosphates to the core particle composition of claim 13;

(b) adding a bioactive agent to the core particle composition; and (c) following steps (a) and (b), either (i) detecting formation of nucleic acids or detecting sizes of nucleic acids found in the core particle composition or (ii) measuring an RNase H activity exhibited by the core particle composition.

18. A non-infectious, recombinant hepadnavirus core particle composition isolated from insect cells transformed with one or more recombinant baculoviruses encoding hepadnavirus core protein and hepadnavirus polymerase, wherein the core particles comprise hepadnavirus polymerase and template nucleic acid encapsidated therein such that, upon addition of deoxynucleoside triphosphates to the composition, the deoxynucleotides are incorporated into DNA.

19. The composition of claim 18, wherein a first recombinant baculovirus encodes the core protein and a second baculovirus encodes the polymerase.

20. The composition of claim 18, wherein the encapsulated nucleic acid includes RNA, and wherein the addition of deoxynucleotides results in (−)-strand synthesis.

21. The composition of claim 18, wherein the addition of deoxynucleotides results in (+)-strand synthesis.

22. A method of identifying bioactive agents that interrupt or inhibit hepadnavirus replication or characterizing the potency of antiviral agents in interrupting or inhibiting hepadnavirus replication, the method comprising (a) adding one or more deoxynucleoside triphosphates to the core particle composition of claim 18;

(b) adding a bioactive agent to the core particle composition; and (c) following steps (a) and (b), either (i) detecting formation of nucleic acids or detecting sizes of nucleic acids found in the core particle composition or (ii) measuring an RNase H activity exhibited by the core particle composition.

23. A non-infectious, recombinant hepadnavirus core particle composition comprising core particles that comprise hepadnavirus polymerase and nucleic acid encapsidated therein such that, upon addition of deoxynucleoside triphosphates to the composition, deoxynucleotides are incorporated into a substantial distribution of (+)-strand nucleic acids.

24. A method of identifying bioactive agents that interrupt or inhibit hepadnavirus replication or characterizing the potency of antiviral agents in interrupting or inhibiting hepadnavirus replication, the method comprising (a) adding one or more deoxynucleoside triphosphates to the core particle composition of claim 23;

(b) adding a bioactive agent to the core particle composition; and (c) following steps (a) and (b), either (i) detecting formation of nucleic acids or detecting sizes of nucleic acids found in the core particle composition or (ii) measuring an RNase H activity exhibited by the core.

25. The method of claim 10 wherein said cells are insect cells and said nucleic acid vectors are baculovirus vectors.

26. The core particle composition of claim 13 wherein said cells are insect cells and said recombinant vectors are baculovirus vectors.

27. The core particle composition of claim 1, wherein said core particles are isolated from insect cells transformed with one or more recombinant baculoviruses.

28. The core particle composition of claim 1, wherein upon addition of deoxynucleoside triphosphates to the composition, the hepadnavirus polymerase incorporates deoxynucleotides into reverse transcripts of the template nucleic acid beginning with the first deoxynucleotide of the reverse transcript.

* * * * *

SEQUENCE LISTING

<160> NUMBER OF SEQ ID NOS: 18

<210> SEQ ID NO 1
<211> LENGTH: 3182
<212> TYPE: DNA
<213> ORGANISM: Hepatitis B Virus

<400> SEQUENCE: 1

```
aattccacaa ccttccacca aactctgcaa gatcccagag tgagaggcct gtatttccct      60
gctggtggct ccagttcagg aacagtaaac cctgttctga ctactgcctc tcccttatcg     120
tcaatcttct cgaggattgg ggaccctgcg ctgaacatgg agaacatcac atcaggattc     180
ctaggacccc ttctcgtgtt acaggcgggg tttttcttgt tgacaagaat cctcacaata     240
ccgcagagtc tagactcgtg gtggacttct ctcaattttc taggggggaac taccgtgtgt     300 cttggccaaa attcgcagtc cccaacctcc aatcactcac caacctcttg tcctccaact     360
tgtcctggtt atcgctggat gtgtctgcgg cgttttatca tcttcctctt catcctgctg     420
ctatgcctca tcttcttgtt ggttcttctg gactatcaag gtatgttgcc cgtttgtcct     480
ctaattccag gatcctcaac aaccagcacg ggaccatgcc ggacctgcat gactactgct     540
caaggaacct ctatgtatcc ctcctgttgc tgtaccaaac cttcggacgg aaattgcacc     600
tgtattccca tcccatcatc ctgggctttc ggaaaattcc tatgggagtg ggcctcagcc     660
cgtttctcct ggctcagttt actagtgcca tttgttcagt ggttcgtagg gctttccccc     720
actgtttggc tttcagttat atggatgatg tggtattggg ggccaagtct gtacagcatc     780
ttgagtccct ttttaccgct gttaccaatt ttctttttgtc tttgggtata catttaaacc     840
ctaacaaaac aaagagatgg ggttactctc taaattttat gggttatgtc attggatgtt     900
atgggtcctt gccacaagaa cacatcatac aaaaaatcaa agaatgtttt agaaaacttc     960
ctattaacag gcctattgat tggaaagtat gtcaacgaat tgtgggtctt ttgggttttg    1020
ctgccccttt tacacaatgt ggttatcctg cgttgatgcc tttgtatgca tgtattcaat    1080
ctaagcaggc tttcactttc tcgccaactt acaaggcctt tctgtgtaaa caatacctga    1140
acctttaccc cgttgcccgg caacgccag gtctgtgcca agtgtttgct gacgcaaccc    1200
ccactggctg gggcttggtc atgggccatc agcgcatgcg tggaaccttt tcggctcctc    1260
tgccgatcca tactgcggaa ctcctagccg cttgttttgc tcgcagcagg tctggagcaa    1320
acattatcgg gactgataac tctgttgtcc tatcccgcaa atatacatcg tttccatggc    1380
```

```
tgctaggctg tgctgccaac tggatcctgc gcgggacgtc ctttgtttac gtcccgtcgg      1440
cgctgaatcc tgcggacgac ccttctcggg gtcgcttggg actctctcgt cccttctcc       1500 gtctgccgtt ccgaccgacc acggggcgca cctctcttta cgcggactcc ccgtctgtgc      1560
cttctcatct gccggaccgt gtgcacttcg cttcacctct gcacgtcgca tggagaccac      1620
cgtgaacgcc caccaaatat tgcccaaggt cttacataag aggactcttg gactctcagc      1680
aatgtcaacg accgaccttg aggcatactt caaagactgt ttgtttaaag actgggagga     1740
gttgggggag gagattaggt taaaggtctt tgtactagga ggctgtaggc ataaattggt      1800
ctgcgcacca gcaccatgca acttttttcac ctctgcctaa tcatctcttg ttcatgtcct    1860
actgttcaag cctccaagct gtgccttggg tggctttggg gcatggacat cgacccttat     1920
aaagaatttg gagctactgt ggagttactc tcgttttttgc cttctgactt ctttccttca    1980
gtacgagatc ttctagatac cgcctcagct ctgtatcggg aagccttaga gtctcctgag    2040
cattgttcac ctcaccatac tgcactcagg caagcaattc tttgctgggg ggaactaatg     2100
actctagcta cctgggtggg tgttaatttg gaagatccag cgtctagaga cctagtagtc     2160
agttatgtca acactaatat gggcctaaag ttcaggcaac tcttgtggtt tcacatttct     2220
tgtctcactt ttggaagaga aacagttata gagtatttgg tgtctttcgg agtgtggatt    2280
cgcactcctc cagcttatag accaccaaat gcccctatcc tatcaacact tccggagact    2340
actgttgtta gacgacgagg caggtcccct agaagaagaa ctcccctcgcc tcgcagacga   2400 aggtctcaat cgccgcgtcg cagaagatct caatctcggg aatctcaatg ttagtattcc    2460
ttggactcat aagtgggga actttactgg gctttattct tctactgtac ctgtctttaa     2520
tcctcattgg aaaacaccat cttttcctaa tatacattta caccaagaca ttatcaaaaa     2580
atgtgaacag tttgtaggcc cactcacagt taatgagaaa agaagattgc aattgattat    2640
gcctgccagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc     2820
accatattct tgggaacaag atctacagca tggggcagaa tctttccacc agcaatcctc    2880
tgggattctt tcccgaccac cagttggatc cagccttcag agcaaacacc gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagtcag    3120
gaaggcagcc taccccgctg tctccacctt tgagaaacac tcatcctcag gccatgcagt    3180
gg                                                                    3182
```

<210> SEQ ID NO 2
<211> LENGTH: 17
<212> TYPE: DNA
<213> ORGANISM: Hepatitis B Virus

<400> SEQUENCE: 2
aactttttca cctctgc                                                    17

<210> SEQ ID NO 3
<211> LENGTH: 61
<212> TYPE: DNA
<213> ORGANISM: Hepatitis B Virus

```
<400> SEQUENCE: 3
tgttcatgtc ctactgttca agcctccaag ctgtgccttg ggtggctttg gggcatggac      60
a                                                                      61

<210> SEQ ID NO 4
<211> LENGTH: 13
<212> TYPE: DNA
<213> ORGANISM: Hepatitis B Virus

<400> SEQUENCE: 4
gaaaaagttg cat                                                         13

<210> SEQ ID NO 5
<211> LENGTH: 35
<212> TYPE: DNA
<213> ORGANISM: Artificial Sequence
<220> FEATURE:
<223> OTHER INFORMATION: PCR primer

<400> SEQUENCE: 5
cccgagctcg gatccttgtt catgtcctac tgttc                                 35

<210> SEQ ID NO 6
<211> LENGTH: 20
<212> TYPE: DNA
<213> ORGANISM: Hepatitis B Virus

<400> SEQUENCE: 6
gcctcgtcgt ctaacaacag                                                  20

<210> SEQ ID NO 7
<211> LENGTH: 33
<212> TYPE: DNA
<213> ORGANISM: Artificial Sequence
<220> FEATURE:
<223> OTHER INFORMATION: PCR primer

<400> SEQUENCE: 7
cccgagctcg gatccaactt tttcacctct gcc                                   33

<210> SEQ ID NO 8
<211> LENGTH: 29
<212> TYPE: DNA
<213> ORGANISM: Artificial Sequence
<220> FEATURE:
<223> OTHER INFORMATION: Mutagenesis oligonucleotide

<400> SEQUENCE: 8
ggattcttgt ctactagaaa aaccccgcc                                        29

<210> SEQ ID NO 9
<211> LENGTH: 32
<212> TYPE: DNA
<213> ORGANISM: Artificial Sequence
<220> FEATURE:
<223> OTHER INFORMATION: Mutagenesis oligonucleotide

<400> SEQUENCE: 9
ccagaagaac ctactagaag atgaggcata gc                                    32

<210> SEQ ID NO 10
<211> LENGTH: 37
<212> TYPE: DNA
<213> ORGANISM: Artificial Sequence
```

```
<220> FEATURE:
<223> OTHER INFORMATION: Oligonucleotide

<400> SEQUENCE: 10
tcgacggatc cataatgccc ctatcctatc aacactt                              37

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide

<400> SEQUENCE: 11
ccggaagtgt tgataggata ggggcattat ggatccg                              37

<210> SEQ ID NO 12
<211> LENGTH: 28
<212> TYPE: DNA
<213> ORGANISM: Artificial Sequence
<220> FEATURE:
<223> OTHER INFORMATION: Mutagenesis oligonucleotide

<400> SEQUENCE: 12
atgtcctact gggcccgcct ccaagctg                                        28

<210> SEQ ID NO 13
<211> LENGTH: 30
<212> TYPE: DNA
<213> ORGANISM: Artificial Sequence
<220> FEATURE:
<223> OTHER INFORMATION: Mutagenesis oligonucleotide

<400> SEQUENCE: 13
accatgcaac ttgggcccct ctgcctaatc                                      30

<210> SEQ ID NO 14
<211> LENGTH: 24
<212> TYPE: DNA
<213> ORGANISM: Hepatitis B Virus

<400> SEQUENCE: 14
tttactgttt tcgtaacagt tttg                                            24

<210> SEQ ID NO 15
<211> LENGTH: 20
<212> TYPE: DNA
<213> ORGANISM: Hepatitis B Virus

<400> SEQUENCE: 15
aggtctttgt actaggaggc                                                 20

<210> SEQ ID NO 16
<211> LENGTH: 20
<212> TYPE: DNA
<213> ORGANISM: Hepatitis B Virus

<400> SEQUENCE: 16
gctaggctgt gctgccaact                                                 20

<210> SEQ ID NO 17
<211> LENGTH: 4
<212> TYPE: PRT
<213> ORGANISM: Hepatitis B Virus
```

-continued

```
<400> SEQUENCE: 17

Tyr Met Asp Asp
1

<210> SEQ ID NO 18
<211> LENGTH: 4
<212> TYPE: PRT
<213> ORGANISM: Artificial Sequence
<220> FEATURE:
<223> OTHER INFORMATION: Mutant

<400> SEQUENCE: 18

Tyr Met His Ala
1
```